US006693122B2

(12) United States Patent
Garvey et al.

(10) Patent No.: US 6,693,122 B2
(45) Date of Patent: Feb. 17, 2004

(54) NITROSATED AND NITROSYLATED POTASSIUM CHANNEL ACTIVATORS, COMPOSITIONS AND METHODS OF USE

(75) Inventors: David S. Garvey, Dover, MA (US); Inigo Saenz de Tejada, Madrid (ES)

(73) Assignee: NitroMed, Inc., Bedford, MA (US)

( * ) Notice: Subject to any disclaimer, the term of this patent is extended or adjusted under 35 U.S.C. 154(b) by 0 days.

(21) Appl. No.: 10/154,916

(22) Filed: May 28, 2002

(65) Prior Publication Data

US 2002/0143188 A1 Oct. 3, 2002

Related U.S. Application Data

(62) Division of application No. 09/570,727, filed on May 12, 2000, now Pat. No. 6,417,207.
(60) Provisional application No. 60/133,888, filed on May 12, 1999.

(51) Int. Cl.[7] ........................ A61K 31/44; C07D 213/72
(52) U.S. Cl. ........................ 514/353; 546/306
(58) Field of Search ........................ 514/353; 546/306

(56) References Cited

U.S. PATENT DOCUMENTS

| | | | |
|---|---|---|---|
| 4,057,636 A | 11/1977 | Petersen | |
| 4,200,640 A | 4/1980 | Nagano et al. | |
| 4,600,577 A | 7/1986 | Didriksen | |
| 4,617,311 A | 10/1986 | Ho | |
| 4,720,387 A | 1/1988 | Sakamoto et al. | |
| 4,769,381 A | 9/1988 | Ishihara et al. | |
| 4,789,679 A | 12/1988 | Hamilton et al. | |
| 4,792,564 A | 12/1988 | Harder et al. | |
| 4,803,213 A | 2/1989 | Iida et al. | |
| 4,822,808 A | 4/1989 | Iida et al. | |
| 4,832,954 A | 5/1989 | Sato et al. | |
| 4,870,090 A | 9/1989 | Noda et al. | |
| 5,032,591 A | 7/1991 | Evans et al. | |
| 5,140,031 A | 8/1992 | Atwal et al. | |
| 5,166,347 A | 11/1992 | Izawa et al. | |
| 5,206,252 A | 4/1993 | Butera et al. | |
| 5,211,943 A | 5/1993 | Azuma et al. | |
| 5,223,508 A | 6/1993 | Izawa et al. | |
| 5,232,938 A | 8/1993 | Stemp et al. | |
| 5,256,688 A | 10/1993 | Grover et al. | |
| 5,262,419 A | 11/1993 | Aberg et al. | |
| 5,354,764 A | 10/1994 | Grover et al. | |
| 5,393,771 A | 2/1995 | Atwal | |
| 5,401,758 A | 3/1995 | Atwal et al. | |
| 5,411,973 A | 5/1995 | Russell et al. | |
| 5,416,097 A | 5/1995 | Erhardt et al. | |
| 5,482,969 A | 1/1996 | Empfield et al. | |
| 5,488,059 A | 1/1996 | Buhl | |
| 5,504,089 A | 4/1996 | Russell | |
| 5,510,386 A | 4/1996 | Empfield et al. | |
| 5,563,160 A | 10/1996 | Bramm et al. | |
| 5,580,576 A | 12/1996 | Veronesi et al. | |
| 5,677,324 A | 10/1997 | Mackenzie et al. | |
| 5,679,706 A | 10/1997 | D'Alonzo et al. | |
| 5,693,639 A | 12/1997 | Empfield et al. | |
| 5,696,140 A | * 12/1997 | Bramm et al. | 514/353 |
| 5,800,385 A | 9/1998 | Demopulos | |
| 5,837,702 A | 11/1998 | Rovnyak et al. | |
| 5,858,017 A | 1/1999 | Demopulos | |
| 5,860,950 A | 1/1999 | Demopulos | |
| 5,900,432 A | 5/1999 | Empfield et al. | |
| 5,972,961 A | 10/1999 | Hewawasam et al. | |
| 6,214,849 B1 | 4/2001 | Saxena et al. | |

FOREIGN PATENT DOCUMENTS

| | | |
|---|---|---|
| DE | 2714713 A1 | 10/1977 |
| DE | 4420523 A1 | 12/1995 |
| EP | 0 076 075 A1 | 4/1983 |
| EP | 0 107 423 A1 | 5/1984 |
| EP | 0 120 427 A1 | 10/1984 |
| EP | 0 120 428 A1 | 10/1984 |
| WO | WO 96/19233 | 6/1996 |
| WO | WO 98/42661 A1 | 10/1998 |
| WO | 9907370 | 2/1999 |
| WO | 9911238 | 3/1999 |
| WO | WO 00/66097 | 11/2000 |

OTHER PUBLICATIONS

Holmquist et al, Acta. Physiol Scand., 138:463–469 (1990).
Holmquist et al, The Journal of Urology, 144:146–151 (1990).
Edwards et al, TiPS, 11:417–422 (1990).
Christ et al, Journal of Andrology, 14(5):319–328 (1993).
Hedlund et al, The Journal of Urology, 151:1107–1113 (1994).

(List continued on next page.)

*Primary Examiner*—Charanjit S. Aulakh
(74) *Attorney, Agent, or Firm*—Hale and Dorr LLP

(57) ABSTRACT

The present invention describes novel nitrosated and/or nitrosylated potassium channel activators, and novel compositions comprising at least one nitrosated and/or nitrosylated potassium channel activator, and, optionally, at least one compound that donates, transfers or releases nitric oxide, elevates endogenous levels of endothelium-derived relaxing factor, stimulates endogenous synthesis of nitric oxide or is a substrate for nitric oxide synthase and/or at least one vasoactive agent. The present invention also provides novel compositions comprising at least one potassium channel activator, and at least one compound that donates, transfers or releases nitric oxide, elevates endogenous levels of endothelium-derived relaxing factor, stimulates endogenous synthesis of nitric oxide or is a substrate for nitric oxide synthase and/or at least one vasoactive agent. The present invention also provides methods for treating or preventing sexual dysfunctions in males and females, for enhancing sexual responses in males and females, and for treating or preventing cardiovascular disorders, cerebrovascular disorders, hypertension, asthma, baldness, urinary incontinence, epilepsy, sleep disorders, gastrointestinal disorders, migraines, irritable bowel syndrome and sensitive skin.

44 Claims, 16 Drawing Sheets

OTHER PUBLICATIONS

Fan et al, The Journal of Urology, 153:818–825 (1995).
Seftel et al, Biochem and Biophys. Res. Comm., 219:382–387 (1996).
Atwal et al, J. Med. Chem., 41:271–275 (1998).
Gupta et al., British Journal of Pharmacology, vol. 116, pp. 2201–2206, (1995).
Thirstrup et al., European Journal of Pharmacology, vol. 326, pp. 191–200; (1997).
Gopalakrishnan et al., Journal of Pharmacology and Experimental Therapeutics, vol. 289, No. 1, pp. 551–558; (1999).
Chemical Abstracts, 101:83562 (1984).
Chemical Abstracts, 128:175873 (1997).
PCT Internation Search Report for PCT/US00/12957 (Aug. 8, 2000).
Shou et al, Bioorganic & Medicinal Chemistry Letters, 7(24):3095–3100 (1997).
Inoue et al, The Journal of Pharmacology and Experimental Therapeutics, 229(3):793–802 (1984).

* cited by examiner

NITROSATED AND NITROSYLATED POTASSIUM CHANNEL ACTIVATORS, COMPOSITIONS AND METHODS OF USE

RELATED APPLICATIONS

This application is a division of Ser. No. 09/570,727 filed May 12, 2000 now U.S. Pat. No. 6,417,207 claims priority to U.S. Provisional Application No. 60/133,888 filed May 12, 1999.

FIELD OF THE INVENTION

The present invention describes novel nitrosated and/or nitrosylated potassium channel activators, and novel compositions comprising at least one nitrosated and/or nitrosylated potassium channel activator, and, optionally, at least one compound that donates, transfers or releases nitric oxide, elevates endogenous levels of endothelium-derived relaxing factor, stimulates endogenous synthesis of nitric oxide or is a substrate for nitric oxide synthase and/or at least one vasoactive agent. The present invention also provides novel compositions comprising at least one potassium channel activator, and at least one compound that donates, transfers or releases nitric oxide, elevates endogenous levels of endothelium-derived relaxing factor, stimulates endogenous synthesis of nitric oxide or is a substrate for nitric oxide synthase and/or at least one vasoactive agent. The present invention also provides methods for treating or preventing sexual dysfunctions in males and females, for enhancing sexual responses in males and females, and for treating or preventing cardiovascular disorders, cerebrovascular disorders, hypertension, asthma, baldness, urinary incontinence, epilepsy, sleep disorders, gastrointestinal disorders, migraines, irritable bowel syndrome, and sensitive skin.

BACKGROUND OF THE INVENTION

Adequate sexual function is a complex interaction of hormonal events and psychosocial relationships. There are four stages to sexual response as described in the *International Journal of Gynecology & Obstetrics*, 51(3):265–277 (1995). The first stage of sexual response is desire. The second stage of sexual response is arousal. Both physical and emotional stimulation may lead to breast and genital vasodilation and clitoral engorgement (vasocongestion). In the female, dilation and engorgement of the blood vessels in the labia and tissue surrounding the vagina produce the "orgasmic platform," an area at the distal third of the vagina where blood becomes sequestered. Localized perivaginal swelling and vaginal lubrication make up the changes in this stage of sexual response. Subsequently, ballooning of the proximal portion of the vagina and elevation of the uterus occurs. In the male, vasodilation of the cavernosal arteries and closure of the venous channels that drain the penis produce an erection. The third stage of sexual response is orgasm, while the fourth stage is resolution. Interruption or absence of any of the stages of the sexual response cycle can result in sexual dysfunction. One study found that 35% of males and 42% of females reported some form of sexual dysfunction. Read et al, *J. Public Health Med.*, 19(4):387–391 (1997).

While there are obvious differences in the sexual response between males and females, one common aspect of the sexual response is the erectile response. The erectile response in both males and females is the result of engorgement of the erectile tissues of the genitalia with blood which is caused by the relaxation of smooth muscles in the arteries serving the genitalia.

In males, some pharmacological methods of treating sexual dysfunctions are available, however, such methods have not proven to be highly satisfactory or without potentially severe side-effects. Papaverine is now widely used to treat impotence. Papaverine is generally effective in cases where the dysfunction is psychogenic or neurogenic and where severe atherosclerosis is not involved. Injection of papaverine, a smooth muscle relaxant, or phenoxybenzamine, a non-specific antagonist and hypotensive, into corpus cavernosum has been found to cause an erection sufficient for vaginal penetration, however, these treatments are not without the serious and often painful side effect of priapism. Also, in cases where severe atherosclerosis is not a cause of the dysfunction, intracavernosal injection of phentolamine, an α-adrenergic antagonist, is used. As an alternative or, in some cases, as an adjunct to α-adrenergic blockade, prostaglandin $E_1$ ($PGE_1$) has been administered via intracavernosal injection. A major side effect frequently associated with intracorprally delivered $PGE_1$ is penile pain and burning.

Potassium channel activators have been developed to treat numerous diseases. For example, Gopalakrishnan et al, *Drug Dev. Res.* 28:95–127 (1993) describe this class of compounds for treating diseases such as hypertension, asthma, hair growth, ischemia and urinary incontinence; U.S. Pat. Nos. 5,256,688 and 5,354,764 disclose the use of pinacidil or cromakalim for treating myocardial ischemia; U.S. Pat. No. 5,262,419 discloses treating ulcerative gastrointestinal conditions; U.S. Pat. No. 4,792,564 discloses treating and preventing cerebral vasospasms; U.S. Pat. No. 4,789,679 discloses treating incontinence; U.S. Pat. No. 4,057,636 discloses the use of potassium channel activators for lowering blood pressure; U.S. Pat. No. 5,869,509 discloses the use of potassium channel activators for treating ischemia, convulsions, asthma, irritable bowel syndrome, migraine, traumatic brain injury, male erectile dysfunction and urinary incontinence; WO 99/11238 discloses the use of potassium channel activators for treating sensitive skin, particularly for the elimination of itching, pruritus, stabbing pains, tingling and/or erythema; Aizawa et al, *J. Cardiovasc. Pharmcol.* 10:S123–S129 (1987) describes the use of nicorandil for treating ischemic heart disease; U.S. Pat. No. 4,617,311 discloses the use of potassium channel activators for treating asthma; and Boselli et al, *Clin. Neuropharmacol* 20(3):252–263 (1997) compares the use of lorazepam with other compounds as sedatives for treating insomnia. The disclosure of each of these patents, applications and publications is incorporated by reference herein in their entirety.

There is a need in the art for new and improved treatments of male and female sexual dysfunctions and other diseases, particularly treatments that do not have the undesirable side effects of those agents currently used. The present invention is directed to these, as well as other, important ends.

SUMMARY OF THE INVENTION

Nitric oxide (NO) has been shown to mediate a number of actions, including the bactericidal and tumoricidal actions of macrophages and blood vessel relaxation of endothelial cells. NO and NO donors have also been implicated as mediators of nonvascular smooth muscle relaxation. As described herein, this effect includes the dilation of the corpus cavernous smooth muscle, an event involved in the sexual response process in both males and females. However, the effects of modified potassium channel activators, which are directly or indirectly linked with a nitric oxide adduct, and which are optionally used in conjunction with NO donors, have not been previously investigated.

In arriving at the present invention, it was unexpectedly discovered that the adverse effects associated with potassium channel activators can be avoided by the use of nitrosated and/or nitrosylated potassium channel activators or by the use of at least one potassium channel activator in combination with at least one nitric oxide donor. Such adverse effects include postural hypotension, headaches, dizziness, palpitations, gastric pain, nausea and vomiting. The smooth muscle relaxant properties of the potassium channel activators and of compounds that donate, release or transfer nitrogen monoxide or elevate levels of endogenous nitric oxide or endothelium-derived relaxing factor (EDRF) or are substrates for nitric oxide synthase work together to permit the same efficacy with lower doses of the potassium channel activators or work synergistically to produce an effect that is greater than the additive effects of the potassium channel activators and the compounds that donate, release or transfer nitrogen monoxide or elevate levels of endogenous nitric oxide or EDRF or is a substrates for nitric oxide synthase.

One aspect of the present invention provides novel nitrosated and/or nitrosylated potassium channel activators. The potassium channel activators can be nitrosated and/or nitrosylated through one or more sites such as oxygen (hydroxyl condensation), sulfur (sulfhydryl condensation), carbon and/or nitrogen. The present invention also provides compositions comprising a therapeutically effective amount of such compounds in a pharmaceutically acceptable carrier.

Another aspect of the present invention provides compositions comprising a therapeutically effective amount of at least one potassium channel activator, that is optionally substituted with at least one NO and/or $NO_2$ group (i.e., nitrosylated and/or nitrosated), and at least one compound that donates, transfers or releases nitrogen monoxide as a charged species, i.e., nitrosonium ($NO^+$) or nitroxyl (NO—), or as the neutral species, nitric oxide (NO.), and/or stimulates endogenous production of nitric oxide or EDRF in vivo and/or is a substrate for nitric oxide synthase. The present invention also provides for such compositions in a pharmaceutically acceptable carrier.

Yet another aspect of the present invention provides compositions comprising a therapeutically effective amount of at least one potassium channel activator, that is optionally substituted with at least one NO and/or $NO_2$ group (i.e., nitrosylated and/or nitrosated), at least one vasoactive drug, and, optionally, at least one compound that donates, transfers or releases nitrogen monoxide as a charged species, i.e., nitrosonium ($NO^+$) or nitroxyl (NO—), or as the neutral species, nitric oxide (NO.), and/or stimulates endogenous production of nitric oxide or EDRF in vivo and/or is a substrate for nitric oxide synthase. The invention also provides for such compositions in a pharmaceutically acceptable carrier.

Yet another aspect of the present invention provides methods for treating and/or preventing sexual dysfunctions and/or enhancing sexual responses in patients, including males and females, by administering to a patient in need thereof a therapeutically effective amount of at least one nitrosated and/or nitrosylated potassium channel activator and, optionally, at least one compound that donates, transfers or releases nitric oxide as a charged species, i.e., nitrosonium ($NO^+$) or nitroxyl (NO—), or as the neutral species, nitric oxide (NO.), and/or stimulates endogenous production of nitric oxide or EDRF in vivo and/or is a substrate for nitric oxide synthase. The methods can further comprise administering a therapeutically effective amount of at least one vasoactive agent. Alternatively, the methods for treating and/or preventing sexual dysfunctions and/or enhancing sexual responses in patients, including males and females, can comprise administering a therapeutically effective amount of at least one nitrosated and/or nitrosylated potassium channel activator, at least one vasoactive agent, and, optionally, at least one compound that donates, transfers or releases nitric oxide as a charged species, i.e., nitrosonium ($NO^+$) or nitroxyl (NO—), or as the neutral species, nitric oxide (NO.), and/or stimulates endogenous production of nitric oxide or EDRF in vivo and/or is a substrate for nitric oxide synthase. The nitrosated and/or nitrosylated potassium channel activators, nitric oxide donors, and/or vasoactive agents can be administered separately or as components of the same composition in one or more pharmaceutically acceptable carriers.

The present invention also provides methods for treating and/or preventing sexual dysfunctions and/or enhancing sexual responses in patients, including males and females, by administering to a patient in need thereof a therapeutically effective amount of at least one potassium channel activator and at least one compound that donates, transfers or releases nitric oxide as a charged species, i.e., nitrosonium ($NO^+$) or nitroxyl (NO—), or as the neutral species, nitric oxide (NO.), and/or stimulates endogenous production of nitric oxide or EDRF in vivo and/or is a substrate for nitric oxide synthase. The methods can further comprise administering a therapeutically effective amount of at least one vasoactive agent. Alternatively, the methods for treating and/or preventing sexual dysfunctions and/or enhancing sexual responses in patients, including males and females, can comprise administering a therapeutically effective amount of at least one potassium channel activator, at least one vasoactive agent, and, optionally, at least one compound that donates, transfers or releases nitric oxide as a charged species, i.e., nitrosonium ($NO^+$) or nitroxyl (NO—), or as the neutral species, nitric oxide (NO.), and/or stimulates endogenous production of nitric oxide or EDRF in vivo and/or is a substrate for nitric oxide synthase. The potassium channel activators, the nitric oxide donors, and the vasoactive agents can be administered separately or as components of the same composition in one or more pharmaceutically acceptable carriers.

The present invention also provides methods using the compounds and compositions described herein to prevent or treat cardiovascular disorders, such as congestive heart failure and myocardial ischemia, especially angina pectoris and arrhythmia; cerebrovascular disorders, including those associated with cerebral ischemia; hypertension; asthma; baldness; urinary incontinence; epilepsy; sleep disorders; gastrointestinal disorders; migraines; irritable bowel syndrome and sensitive skin, by administering to a patient in need thereof a therapeutically effective amount of at least one of the compounds and/or compositions described herein. In these methods, the potassium channel activators that are optionally nitrosated and/or nitrosylated, nitric oxide donors and vasoactive agents can be administered separately or as components of the same composition in one or more pharmaceutically acceptable carriers.

These and other aspects of the present invention are described in detail herein.

DETAILED DESCRIPTION OF THE INVENTION

Figure 1:
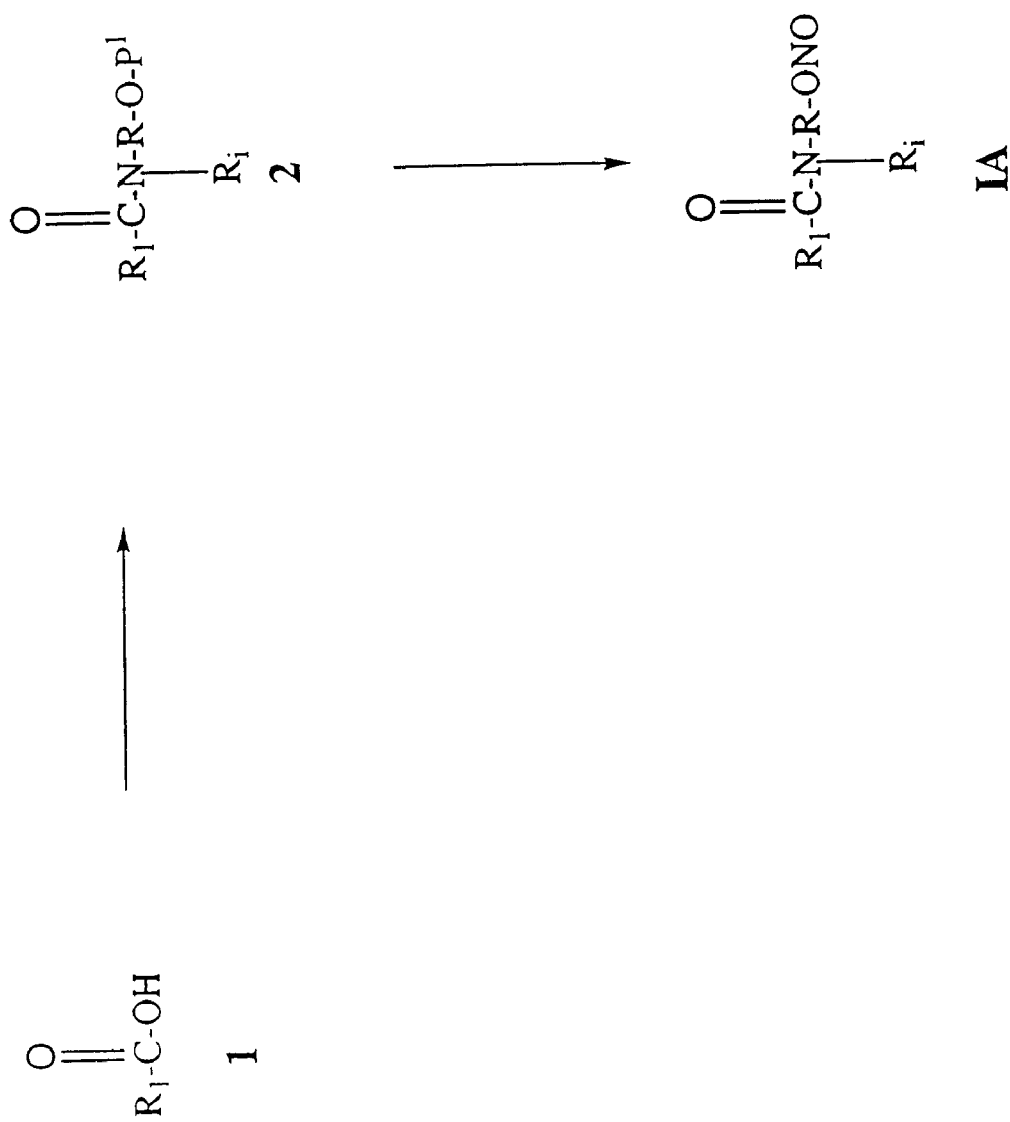
FIG. 1 is the synthetic scheme for the preparation of a nitrite containing N-amide of Formula (I).

As used throughout the disclosure, the following terms, unless otherwise indicated, shall be understood to have the following meanings.

"Potassium channel activator" refers to any compound that results in the opening of the potassium channel such that the permeability of potassium is increased, thereby resulting in hyperpolarization and relaxation of smooth muscles.

"Patient" refers to animals, preferably mammals, more preferably humans, and includes children and adults.

"Gastrointestinal disorder" refers to any disease or disorder of the upper gastrointestinal tract of a patient including, for example, peptic ulcers, stress ulcers, gastric hyperacidity, dyspepsia, gastroparesis, Zollinger-Ellison syndrome, gastroesophageal reflux disease, short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns.

"Upper gastrointestinal tract" refers to the esophagus, the stomach, the duodenum and the jejunum.

"Ulcers" refers to lesions of the upper gastrointestinal tract lining that are characterized by loss of tissue. Such ulcers include gastric ulcers, duodenal ulcers and gastritis.

"Thromboxane inhibitor" refers to any compound that reversibly or irreversibly inhibits thromboxane synthesis, and includes compounds which are the so-called thromboxane $A_2$ receptor antagonists, thromboxane $A_2$ antagonists, thromboxane $A_2$/prostaglandin endoperoxide antagonists, thromboxane receptor (TP) antagonists, thromboxane antagonists, thromboxane synthase inhibitors, and dual acting thromboxane synthase inhibitors and thromboxane receptor antagonists.

"Thromboxane $A_2$ receptor antagonist" refers to any compound that reversibly or irreversibly blocks the activation of any thromboxane $A_2$ receptor.

"Thromboxane synthase inhibitor" refers to any compound that reversibly or irreversibly inhibits the enzyme thromboxane synthesis thereby reducing the formation of thromboxane $A_2$.

"Dual acting thromboxane receptor antagonist and thromboxane synthase inhibitor" refers to any compound that simultaneously acts as a thromboxane $A_2$ receptor antagonist and a thromboxane synthase inhibitor.

"Topical" refers to the delivery of a compound by passage through the skin and into the blood stream and includes transdermal delivery.

"Transmucosal" refers to delivery of a compound by passage of the compound through the mucosal tissue and into the blood stream.

"Transurethral" or "intraurethral" refers to delivery of a drug into the urethra, such that the drug contacts and passes through the wall of the urethra and enters into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO—$, $NO.$), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, $NO—$, $NO.$), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo.

"NO donor" also includes compounds that are substrates for nitric oxide synthase.

"Alkyl" refers to a lower alkyl group, a haloalkyl group, an alkenyl group, an alkynyl group, a bridged cycloalkyl group, a cycloalkyl group or a heterocyclic ring, as defined herein.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2-C_{10}$ hydrocarbon (preferably a $C_2-C_8$ hydrocarbon, more preferably a $C_2-C_6$ hydrocarbon) which can comprise one or more carbon—carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Alkynyl" refers to an unsaturated acyclic $C_2-C_{10}$ hydrocarbon (preferably a $C_2-C_8$ hydrocarbon, more preferably a $C_2-C_6$ hydrocarbon) which can comprise one or more carbon—carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo[3.3.0] octane, 7-oxabycyclo[2.2.1]heptyl, 8-azabicyclo[3,2,1]oct-2-enyl and the like.

"Cycloalkyl" refers to a saturated or unsaturated cyclic hydrocarbon comprising from about 3 to about 8 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo and nitro. Exemplary cycloalkyl groups include cyclopropyl, cyclobutyl, cyclopentyl, cyclohexyl, cyclohexenyl, cyclohepta,1,3-dienyl, and the like.

"Heterocyclic ring or group" refers to a saturated, unsaturated, cyclic or aromatic or polycyclic hydrocarbon group having about 3 to about 12 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylamino, dialkylamino, arylamino, diarylamino, alkylarylamino, hydroxy, oxo, thial, halo, carboxyl, carboxylic ester, alkylcarboxylic acid, alkylcarboxylic ester, aryl, arylcarboxylic acid, arylcarboxylic ester, amidyl, ester, carboxamido, alkylcarboxamido, arylcarboxamido, sulfonic acid, sulfonic ester, sulfonamido and nitro. Exemplary heterocyclic groups include pyrrolyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, 2-pyrrolinyl, 3-pyrrolinyl, pyrrolindinyl, oxazolindinyl 1,3-dioxolanyl, 2,6-dioxabicyclo[3,3,0]octanyl, 2-imidazonlinyl, imidazolindinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicylic aryl groups) can be unsubstituted or substituted with one, two or three substituents independently selected from alkyl, alkoxy, amino, alkylamino, dialkylamino, arylamino, diarylamino, alkylarylamino, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein.

"Cycloalkylalkyl" refers to a cycloalkyl radical, as defined herein, attached to an alkyl radical, as defined herein.

"Heterocyclicalkyl" refers to a heterocyclic ring radical, as defined herein, attached to an alkyl radical, as defined herein.

"Cycloalkenyl" refers to an unsaturated cyclic hydrocarbon having about 3 to about 10 carbon atoms (preferably about 3 to about 8 carbon atoms, more preferably about 3 to about 6 carbon atoms) comprising one or more carbon—carbon double bonds.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkoxy" refers to $R_{50}O$—, wherein $R_{50}$ is an alkyl group, as defined herein. Exemplary alkoxy groups include methoxy, ethoxy, t-butoxy, cyclopentyloxy, and the like.

"Arylalkoxy or alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}$ O—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Haloalkoxy" refers to a haloalkyl group, as defined herein, to which is appended an alkoxy group, as defined herein. Exemplary haloalkyl groups include 1,1,1-trichloroethoxy, 2-bromobutoxy, and the like.

"Hydroxy" refers to —OH.

"Oxo" refers to =O.

"Oxy" refers to —O$^-$R$_{77}^+$ wherein $R_{77}$ is an organic or inorganic cation.

"Organic cation" refers to a positively charged organic ion. Exemplary organic cations include alkyl substituted ammonium cations, and the like.

"Inorganic cation" refers to a positively charged metal ion. Exemplary inorganic cations include metal cations such as for example, sodium, potassium, calcium, and the like.

"Hydroxyalkyl" refers to a hydroxy group, as defined herein, appended to an alkyl group, as defined herein.

"Amino" refers to —NH$_2$.

"Nitrate" refers to —O—NO$_2$.

"Nitrite" refers to —O—NO.

"Thionitrate" refers to —S—NO$_2$.

"Thionitrite" and "nitrosothiol" refer to —S—NO.

"Nitro" refers to the group —NO$_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Alkylamino" refers to $R_{50}$NH—, wherein $R_{50}$ is an alkyl group, as defined herein. Exemplary alkylamino groups include methylamino, ethylamino, butylamino, cyclohexylamino, and the like.

"Arylamino" refers to $R_{55}$NH—, wherein $R_{55}$ is an aryl group, as defined herein.

"Dialkylamino" refers to $R_{50}R_{52}$N—, wherein $R_{50}$ and $R_{52}$ are each independently an alkyl group, as defined herein. Exemplary dialkylamino groups include dimethylamino, diethylamino, methyl propargylamino, and the like.

"Diarylamino" refers to $R_{55}R_{60}$N—, wherein $R_{55}$ and $R_{60}$ are each independently an aryl group, as defined herein.

"Alkylarylamino" refers to $R_{50}R_{55}$N—, wherein $R_{50}$ is an alkyl group, as defined herein, and $R_{55}$ is an aryl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein.

"Aminoaryl" refers to an amino group, an alkylamino group, a dialkylamino group, an arylamino group, a diarylamino group, an alkylarylamino group or a heterocyclic ring, as defined herein, to which is appended an aryl group, as defined herein.

"Thio" refers to —S—.

"Sulfinyl" refers to —S(O)—.

"Methanthial" refers to —C(S)—.

"Thial" refers to =S.

"Sulfonyl" refers to —S(O)$_2^-$.

"Sulfonic acid" refers to —S(O)$_{2O}$R$_{76}$, wherein $R_{76}$ is a hydrogen, an organic cation or an inorganic cation.

"Alkylsulfonic acid" refers to a sulfonic acid group, as defined herein, appended to an alkyl group, as defined herein.

"Arylsulfonic acid" refers to an sulfonic acid group, as defined herein, appended to an aryl group, as defined herein.

"Sulfonic ester" refers to —S(O)$_{2O}$R$_{58}$, wherein $R_{58}$ is an alkyl group, an aryl group, an alkylaryl group or an aryl heterocyclic ring, as defined herein.

"Sulfonamido" refers to —S(O)$_2$—N(R$_{51}$)(R$_{57}$), wherein $R_{51}$ and $R_{57}$ are each independently a hydrogen atom, an alkyl group, an aryl group, an alkylaryl group, or an aryl-heterocyclic ring, as defined herein, or $R_{51}$, and $R_{57}$ taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}$S—, wherein $R_{50}$ is an alkyl group, as defined herein.

"Arylthio" refers to $R_{55}$S—, wherein $R_{55}$ is an aryl group, as defined herein.

"Cycloalkylthio" refers to $R_{54}$S—, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Alkylsulfinyl" refers to $R_{50}$—S(O)—, wherein $R_{50}$ is an alkyl group, as defined herein.

"Alkylsulfonyl" refers to $R_{50}$—S(O)$_2$—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—S(O)$_2$—, wherein $R_{55}$ is an aryl group, as defined herein.

"Amidyl" refers to $R_{51}$C(O)N(R$_{57}$)— wherein $R_{51}$ and $R_{57}$ are each independently a hydrogen atom, an alkyl group, an aryl group, an alkylaryl group, or an arylheterocyclic ring, as defined herein.

"Ester" refers to $R_{51}$C(O)O— wherein $R_{51}$ is a hydrogen atom, an alkyl group, an aryl group, an alkylaryl group, or an arylheterocyclic ring, as defined herein.

"Carbamoyl" refers to —O—C(O)N(R$_{51}$)(R$_{57}$), wherein $R_{51}$ and $R_{57}$ are each independently a hydrogen atom, an alkyl group, an aryl group, an alkylaryl group or an aryl-heterocyclic ring, as defined herein, or $R_{51}$ and $R_{57}$ taken together are a heterocyclic ring, a cycloalkyl group or a bridged cycloalkyl group, as defined herein.

"Carbamate" refers to $R_{51}$O—C(O)N(R$_{57}$), wherein $R_{51}$ and $R_{57}$ are each independently a hydrogen atom, an alkyl group, an aryl group, an alkylaryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to —C(O)OR$_{76}$, wherein $R_{76}$ is a hydrogen, an organic cation or an inorganic cation, as defined herein.

"Carbonyl" refers to —C(O)—.

"Alkylcarbonyl" or "alkanoyl" refers to $R_{50}$—C(O)—, wherein $R_{50}$ is an alkyl group, as defined herein.

"Arylcarbonyl" or "aroyl" refers to $R_{55}$—C(O)—, wherein $R_{55}$ is an aryl group, as defined herein.

"Carboxylic ester" refers to —C(O)OR$_{58}$, wherein $R_{58}$ is an alkyl group, an aryl group, an alkylaryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to —C(O)N($R_{51}$)($R_{57}$), wherein $R_{51}$ and $R_{57}$ are each independently a hydrogen atom, an alkyl group, an aryl group, an alkylaryl group or an arylheterocyclic ring, as defined herein, or $R_{51}$ and $R_{57}$ taken together with the nitrogen to which they are attached form a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N($R_{59}$)—C(O)N($R_{51}$)($R_{57}$) wherein $R_{51}$, $R_{57}$, and $R_{59}$ are each independently a hydrogen atom, an alkyl group, an aryl group, an alkylaryl group, or an arylheterocyclic ring, as defined herein, or $R_{51}$ and $R_{57}$ taken together with the nitrogen to which they are attached form a heterocyclic ring, as defined herein.

"Phosphoryl" refers to —P($R_{70}$)($R_{71}$)($R_{72}$), wherein $R_{70}$ is a lone pair of electrons, sulfur or oxygen, and $R_{71}$ and $R_{72}$ are each independently a covalent bond, a hydrogen, a lower alkyl, an alkoxy, an alkylamino, a hydroxy or an aryl, as defined herein.

The term "sexual dysfunction" generally includes any sexual dysfunction in a patient, including an animal, preferably a mammal, more preferably a human. The patient can be male or female. Sexual dysfunctions can include, for example, sexual desire disorders, sexual arousal disorders, orgasmic disorders and sexual pain disorders. Female sexual dysfunction refers to any female sexual dysfunction including, for example, sexual desire disorders, sexual arousal dysfunctions, orgasmic dysfunctions, sexual pain disorders, dyspareunia, and vaginismus. The female can be pre-menopausal or menopausal. Sexual dysfunction can be caused, for example, by pregnancy, menopause, cancer, pelvic surgery, chronic medical illness or medications. Male sexual dysfunction refers to any male sexual dysfunctions including, for example, male erectile dysfunction and impotence.

The present invention is directed to the treatment and/or prevention of sexual dysfunctions in patients, including males and females, by administering the compounds and compositions described herein. The present invention is also directed to enhancing sexual responses in patients, including males and females, by administering the compounds and/or compositions described herein. The novel compounds and novel compositions of the present invention are described in more detail herein.

Potassium channel activators have the ability to open potassium channels in a variety of cells. Opening of the potassium channel leads to hyperpolarization of the surface membrane with consequent closure of voltage-dependent ion channels and reduction of free intracellular potassium ions. The potassium channel activators have a high affinity for potassium channels of vascular smooth muscle. Vasodilation and a reduction in systemic vascular resistance are their predominant pharmacological effects. Coronary, cerebral, airway and corpus cavernosum arteries are very sensitive to potassium channel activator-induced dilation. The potassium channel activator, nicorandil, is marketed by Rhone-Poulenc-Rorer under the trademark ICOREL™. Holmquist et al, *Acta. Physiol. Scand.*, 138:463–469 (1990) investigated the effects of pinacidil on isolated human corpus cavernosum tissue, and their results suggest that pinacidil is effective in relaxing the tissue, probably by increasing the potassium permeability and subsequent hyperpolarization.

Contemplated potassium channel activators for use in the present invention include all those known in the art, such as, for example, nicorandil, pinacidil, cromakalim (BRL 34915), aprikalim, bimakalim, emakalim, lemakalim, minoxidil, diazoxide, 9-chloro-7-(2-chlorophenyl)-5H-pyrimido(5,4,-d)(2)-benzazepine, Ribi, CPG11952, CGS-9896, ZD 6169, diazixide, Bay X 9227, P1075, Bay X 9228, SDZ PCO 400, WAY-120,491, WAY-120,129, Ro 31-6930, SR 44869, BRL 38226, S 0121, SR 46142A, CGP 42500, SR 44994, artilide fumarate, lorazepam, temazepam, rilmazafone, nimetazepam, midazolam, lormetazepam, loprazolam, ibutilide fumarate, haloxazolam, flunitrazepam, estazolam, doxefazepam, clonazepam, cinolazepam and brotizolam. Preferred potassium channel activators for use in the methods described herein (particularly for the treatment and/or prevention of sexual dysfunctions) are nicorandil, pinacidil, cromakalim (BRL 34915), aprikalim, bimakalim, emakalim and lemakalim. Nicorandil, pinacidil, cromakalim and minoxidil are the most preferred potassium channel activators.

Sources of information for the above compounds include Goodman and Gilman, The Pharmacological Basis of Therapeutics (9th Ed.), McGraw-Hill, Inc. (1996), The Physician's Desk Reference (49th Ed.), Medical Economics (1995), Drug Facts and Comparisons (1993 Ed), Facts and Comparisons (1993), Merck Index on CD-ROM, Twelfth Edition, Version 12:1, (1996), STN Express, file phar and file registry, the disclosures of each of which are incorporated herein by reference in their entirety.

In addition to the specific potassium channel activators described herein, the potassium channel activators for use in the present invention generally include compounds of Formula (A), Formula (B), Formula (C), Formula (D), Formula (E) and Formula (F).

The potassium channel activator of Formula (A) is:

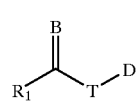

(A)

wherein $R_1$ is:

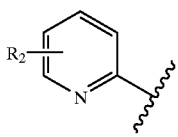
(1)

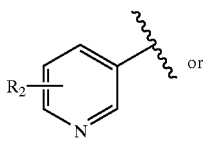 or
(2)

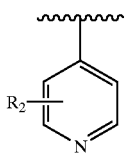
(3)

wherein $R_2$ is a hydrogen atom or a halogen atom;

B is oxygen or —N—CN; and

D is A or J;

A is —$W_a$-$E_b$-$(C(R_e)(R_f))_p$-$E_c$-$(C(R_e)(R_f))_x$—$W_d$—$(C(R_e)(R_f))_y$—$W_i$-$E_j$-$W_g$—$(C(R_e)(R_f))_x$—$ONO_2$;

J is —$W_a$-$E_b$-$(C(R_e)(R_f))_p$-$E_c$-$(C(R_e)(R_f))_x$—$W_d$—$(C(R_e)(R_f))_y$—$W_i$-$E_j$-$W_g$—$(C(R_e)(R_f)(R_h))_z$;

a, b, c, d, g, i and j are each independently an integer from 0 to 3;

p, x, y and z are each independently an integer from 0 to 10;

W at each occurrence is independently —C(O)—, —C(S)—, —T-, —$(C(R_e)(R_f))_h$—, an alkyl group, an aryl group, a heterocyclic ring, an arylheterocyclic ring, or —$(CH_2CH_2O)_q$—;

E at each occurrence is independently —T-, an alkyl group, an aryl group, —$(C(R_e)(R_f))_h$—, a heterocyclic ring, an arylheterocyclic ring, or —$(CH_2CH_2O)_q$—;

h is an integer form 1 to 10;

q is an integer from 1 to 5;

$R_e$, $R_f$ and $R_h$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, or $R_e$ and $R_f$ or $R_e$, $R_f$ and $R_h$ taken together with the carbons to which they are attached form a carbonyl, a methanthial, a heterocyclic ring, a cycloalkyl group or a bridged cycloalkyl group;

k is an integer from 1 to 3;

T at each occurrence is independently a covalent bond, a carbonyl, an oxygen, —$S(O)_o$— or —$N(R_a)R_i$—;

o is an integer from 0 to 2;

$R_a$ is a lone pair of electrons, a hydrogen or an alkyl group;

$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl.

In cases where $R_e$, $R_f$ and $R_h$ are a heterocyclic ring or taken together $R_e$ and $R_f$ or $R_e$, $R_f$ and $R_h$ are a heterocyclic ring, then $R_i$ can be a substituent on any disubstituted nitrogen contained within the radical where $R_i$ is as defined herein.

In cases where multiple designations of variables which reside in sequence are chosen as a "covalent bond" or the integer chosen is 0, the intent is to denote a single covalent bond connecting one radical to another. For example, $E_0$ would denote a covalent bond, while $E_2$ denotes (E—E) and $(C(R_e)(R_f))_2$ denotes —$C(R_e)(R_f)$—$C(R_e)(R_f)$—, where $R_e$ and $R_f$ at each occurrence are each independently selected from those moieties defined herein.

The potassium channel activator of Formula (B) is:

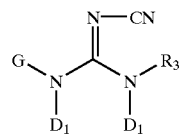
(B)

wherein $R_3$ is a hydrogen, an alkyl, an aryl, an alkylaryl;

$D_1$ is a hydrogen atom or an alkyl group; and

G is:

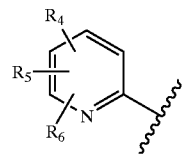
(1)

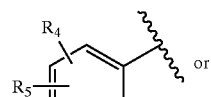 or
(2)

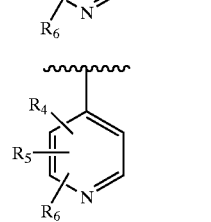
(3)

wherein $R_4$, $R_5$, and $R_6$ are each independently a hydrogen, a halogen, a hydroxy, a lower alkyl, an alkoxy, a nitrite, a nitrite, a carboxyamido, a carboxylic ester, an alkylsulfinyl, an arylsulfinyl, an aminoalkyl, an alkylthio, an arylthio; or $R_5$ and $R_6$ taken together are a group which forms a ring with the two carbon atoms to which they are attached, wherein the group is $-S(O)_t-(CH_2)_r-CH_2-$, $-C(O)Z-(CH_2)_o-CH_2-$, or $-C(O)-CH_2-(CH_2)_o-Z-$;

t is an integer of 1 or 2;
r is an integer from 1 to 3;
Z is oxygen, $NR_7$ or $CH_2$;
$R_7$ is hydrogen or $R_3$; and
o is as defined herein.

The potassium channel activator of Formula (C) is:

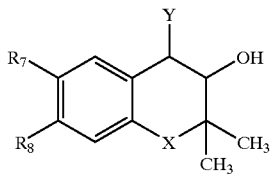
(C)

wherein
X $-(CH_2)_a-$ or oxygen;
Y is:

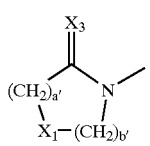
(a)

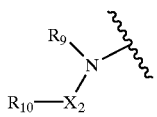
(b)

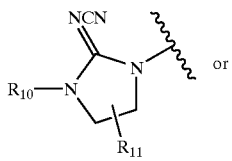
(c)

(d)

$R_7$ and $R_8$ are each independently a hydrogen, an alkylcarbonyl, an alkoxycarbonyl, a heterocyclic ring, an ester, a nitro, a cyano, a halo, a haloalkyl, an alkylsulphinyl, an alkylsulphonyl, a sulfonic ester, an amidyl, a carbamate, a formyl, a sulfonamido, or a carboxamido;

$R_9$ is an aryl or a heterocyclic ring;

$R_{10}$ is a carboxylic ester, a carboxylic acid, a carboxamido, a urea, a thiourea, an amidyl, a sulfamoyl, a hydroxyalkyl, $-C(O)OD$, $-N(R_{59})(C=NCN)NR_{51}R_{57}$, $-N(R_{59})(C=NCN)SR_2$, $-N(R_{59})(C=NCN)OR_{12}$, $-P(O)(OR_{50})_2$, $-P(O)(O(CH_2)_kO)$, $-SR_{11}$, $-S(O)R_{11}$, $-S(O)_2R_{11}$, $-OR_{11}$, a cyano, a heterocyclic ring, a pyridine N-oxide or $-C(NR_{51}R_{57})=CH-C(O)R_{59}$;

$R_{11}$ is a hydrogen, an alkyl, an aryl, an arylalkyl, a cycloalkyl, or cycloalkylalkyl;

$R_{12}$ is an alkyl, an aryl, an alkylaryl, or an arylheterocyclic ring;

$R_{13}$ is aryl, a heterocyclic ring, a cycloalkyl;

$X_1$ is an oxygen, a sulfur, or $-NH-$;
$X_2$ is a hydrogen or an alkyl group;
$X_3$ is oxygen or sulfur;
k' is an interger from 2 to 4;
a' and b' are each independently an integer from 0 to 3; and
a, D, $R_{50}$, $R_{51}$, $R_{57}$ and $R_{59}$ are as defined herein.

The potassium channel activator of Formula (D) is:

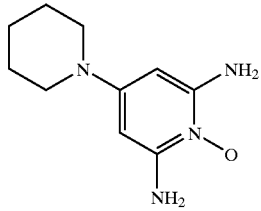
(D)

The potassium channel activator of Formula (E) is:

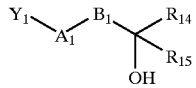
(E)

wherein,
$R_{14}$ and $R_{15}$ are each independently a lower alkyl, a lower haloalkyl or $R_{14}$ and $R_{15}$ together with the carbon to which they are attached form a cyclic haloalkyl group;
$A_1-B_1$ is $-NHC(O)-$, $-OCH_2-$, $-SCH_2-NHCH_2$, $-CH=CH-$, or $-CH=CH-$; and
$Y_1$ is an aryl group.

The potassium channel activator of Formula (F) is:

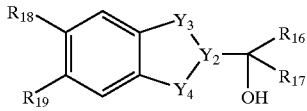
(F)

wherein,
$R_{16}$ and $R_{17}$ are each independently a lower alkyl, a lower haloalkyl or $R_{16}$ and $R_{17}$ together with the carbon to which they are attached form a cyclic haloalkyl group;
$Y_3$ is an sp²-hybridized atom and $Y_2$, $Y_3$, and $Y_4$ together with the carbon atoms to which they are attached form a 5- or 6-membered heterocyclic ring;
$R_{18}$ and $R_{19}$ are each independently a hydrogen, a nitro, a cyano, a halo, a haloalkyl, an alkylsulfonyl, or an aryl, with the proviso that either $R_{18}$ or $R_{19}$ must be a hydrogen but that both $R_{18}$ and $R_{19}$ cannot be a hydrogen.

Other potassium channel activators that can be used in the present invention include those described in U.S. Pat. Nos. 4,057,636, 4,200,640, 5,166,347, 5,223,508, 5,262,419 and 5,869,509 the disclosures of each of which are incorporated by reference herein in their entirety. Methods for making potassium channel activators, including those of Formula (A), Formula (B), Formula (C), Formula (D), Formula (E) and Formula (F) are known in the art, and are described, for example, in U.S. Pat. Nos. 3,382,247, 3,644,364, 4,057,636, 4,200,640, 5,140,031, 5,166,347, 5,206,252, 5,223,508, 5,232,938, 5,262,419, 5,393,771, 5,401,758, 5,411,973, 5,416,097, 5,482,969, 5,504,089, 5,677,324, 5,679,706, 5,693,639, 5,837,702 and 5,900,432 and in EP 0 076 075 A1, EP 0 107 423 A1, EP 0 120 427 A1, EP 0 120 428 A1 and EP 0 107 423 A1, the disclosures of each of which are incorporated by reference herein in their entirety.

The present invention also describes novel nitrosated and/or nitrosylated potassium channel activators of Formula (I):

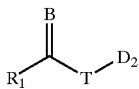
(I)

wherein
$R_1$ is:

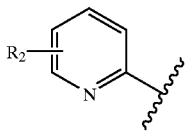
(1)

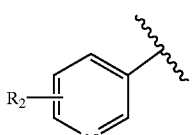
(2)

or

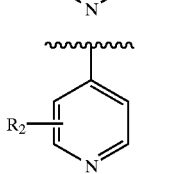
(3)

wherein
$R_2$ is a hydrogen atom or a halogen atom;
B is oxygen or —N—CN;
$D_2$ is Q or K;
Q is —NO or —NO$_2$;
K is —$W_a$-$E_b$-(C($R_e$)($R_f$))$_p$-$E_c$-(C($R_e$)($R_f$))$_x$—$W_d$—(C($R_e$)($R_f$))$_y$—$W_i$-$E_j$-$W_g$(C($R_e$)($R_f$))$_z$-T-Q;
a, b, c, d, g, i and j are each independently an integer from 0 to 3;
p, x, y and z are each independently an integer from 0 to 10;
W at each occurrence is independently —C(O)—, —C(S)—, —T-, —(C($R_e$)($R_f$))$_h$—, an alkyl group, an aryl group, a heterocyclic ring, an arylheterocyclic ring, or —(CH$_2$CH$_2$O)$_q$—;
E at each occurrence is independently —T-, an alkyl group, an aryl group, —(C($R_e$)($R_f$))$_h$—, a heterocyclic ring, an arylheterocyclic ring, or —(CH$_2$CH$_2$O)$_q$—;
h is an integer from 1 to 10;
q is an integer from 1 to 5;
$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, -T-Q, or (C($R_e$)($R_f$))$_k$-T-Q, or $R_e$ and $R_f$ taken together with the carbons to which they are attached form a carbonyl, a methanthial, a heterocyclic ring, a cycloalkyl group or a bridged cycloalkyl group;
k is an integer from 1 to 3;
T at each occurrence is independently a covalent bond, a carbonyl, an oxygen, —S(O)$_o$— or —N($R_a$)$R_i$—;
o is an integer from 0 to 2;
$R_a$ is a lone pair of electrons, a hydrogen or an alkyl group;
$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$—C(T-Q)($R_e$)($R_f$), or —(N$_2$O$_2$—)$^-$.M$^+$, wherein M$^+$ is an organic or inorganic cation; with the proviso that when $R_i$ is —CH$_2$—C(T-Q)($R_e$)($R_f$) or —(N$_2$O$_2$)$^-$.M$^+$, or Re or $R_f$ are T-Q or (C($R_e$)($R_f$))$_k$-T-Q, then the "-T-Q" subgroup can be a hydrogen, an alkyl, an alkoxy, an alkoxyalkyl, an aminoalkyl, a hydroxy, a heterocyclic ring or an aryl group; with the proviso that when the T in "-T-Q" is oxygen then Q is not —NO$_2$; and the compounds of Formula (I) must contain at least one nitrite, nitrate, thionitrite or thionitrate group.

In a preferred embodiment of the present invention, the "-T-D$_2$" group in Formula (I) is not N'-(2-nitroxyethyl), N'-(3-nitroxypropyl), N'-(4-nitrobenzyl), N'-(2-(4-nitrophenyl)-2-nitroxyethyl) or N'-(1-methyl-2-(4-nitrophenyl)-2-nitroxyethyl).

In cases where $R_e$ and $R_f$ are a heterocyclic ring or taken together $R_e$ and $R_f$ are a heterocyclic ring, then $R_i$ can be a substituent on any disubstituted nitrogen contained within the radical where $R_i$ is as defined herein.

In cases where multiple designations of variables which reside in sequence are chosen as a "covalent bond" or the integer chosen is 0, the intent is to denote a single covalent bond connecting one radical to another. For example, $E_0$ would denote a covalent bond, while $E_2$ denotes (E—E) and (C($R_e$)($R_f$))$_2$ denotes —C($R_e$)($R_f$)—C($R_e$)($R_f$)—, where $R_e$ and $R_f$ at each occurrence are each independently selected from those moieties defined herein.

Another embodiment of the present invention describes novel nitrosated and/or nitrosylated potassium channel activators of Formula (II):

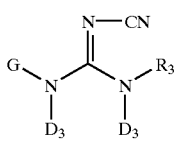
(II)

wherein $R_3$ is a hydrogen, an alkyl, an aryl, an alkylaryl or K;
$D_3$ is a hydrogen or $D_2$, with the proviso that at least one $D_3$ must be designated as $D_2$ if $R_3$ is not K;
G is:

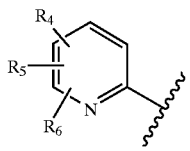
(1)

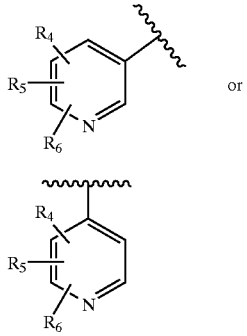

$R_4$, $R_5$, and $R_6$ are each independently a hydrogen, a halogen, a hydroxy, a lower alkyl, an alkoxy, a nitrite, a nitrite, a carboxyamido, a carboxylic ester, an alkylsulfinyl, an arylsulfinyl, an aminoalkyl, an alkylthio, or an arylthio; or $R_5$ and $R_6$ taken together are a group which forms a ring with the two carbon atoms to which they are attached, wherein the group is —S(O)$_o$—(CH$_2$)$_r$—CH$_2$—, —C(O)Z-(CH$_2$)$_o$—CH$_2$, or —C(O)—CH$_2$—(CH$_2$)$_o$—Z-;

t is an integer of 1 or 2;
r is an integer from 1 to 3;
Z is oxygen, $NR_7$ or $CH_2$;
$R_7$ is hydrogen or $R_3$; and
o and $D_2$ are as defined herein.

Another embodiment of the present invention describes novel nitrosated and/or nitrosylated potassium channel activators of Formula (III):

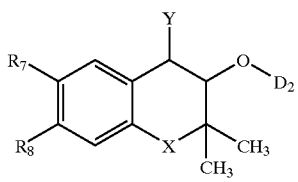
(III)

wherein
X —(CH$_2$)$_a$— or oxygen;
Y is:

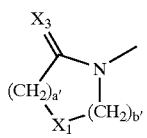
(a)

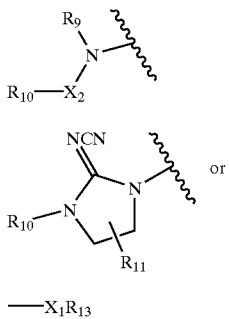
(b)

(c)

or (d)

—X$_1$R$_{13}$ $R_7$ and $R_8$ are each independently a hydrogen, an alkylcarbonyl, an alkoxycarbonyl, a heterocyclic ring, an ester, a nitro, a cyano, a halo, a haloalkyl, an alkylsulphinyl, an alkylsulphonyl, a sulfonic ester, an amidyl, a carbamate, a formyl, a sulfonamido, or a carboxamido;

$R_9$ is an aryl or a heterocyclic ring;
$R_{10}$ is a carboxylic ester, a carboxylic acid, a carboxamido, a urea, a thiourea, an amidyl, a sulfamoyl, a hydroxyalkyl, —C(O)OD, —N(R$_{59}$)(C=NCN)NR$_{51}$R$_{57}$, —N(R$_{59}$)(C=NCN)SR$_{12}$, —N(R$_{59}$)(C=NCN)OR$_{12}$, —P(O)(OR$_{50}$)2, —P(O)(O(CH$_2$)$_k$O), —SR$_{11}$, —S(O)R$_{11}$, —S(O)$_2$R$_{11}$, —OR$_{11}$, a cyano, a heterocyclic ring, a pyridine N-oxide or —C(NR$_{51}$R$_{57}$)=CH—C(O)R$_{59}$;

$R_{11}$ is a hydrogen, an alkyl, an aryl, an arylalkyl, a cycloalkyl, or cycloalkylalkyl;
$R_{12}$ is an alkyl, an aryl, an alkylaryl, or an arylheterocyclic ring;
$R_{13}$ is aryl, a heterocyclic ring, a cycloalkyl;
$X_1$ is an oxygen, a sulfur, or —NH—;
$X_2$ is a hydrogen or an alkyl group;
$X_3$ is oxygen or sulfur;
k' is an interger from 2 to 4;
a' and b' are each independently an integer from 0 to 3; and
a, D, $D_2$, $R_{50}$, $R_{51}$, $R_{57}$ and $R_{59}$ are as defined herein.

Another embodiment of the present invention describes novel nitrosated and/or nitrosylated potassium channel activators of Formula (IV):

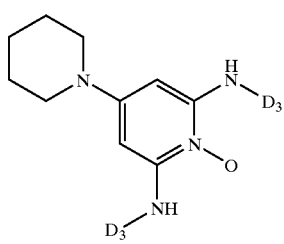
(IV)

wherein,
$D_3$ is hydrogen or $D_2$ with the proviso that at least one $D_3$ must be $D_2$; and
$D_2$ is as defined herein.

Another embodiment of the present invention describes novel nitrosated and/or nitrosylated potassium channel activators of Formula (V):

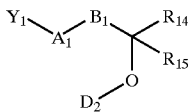

V wherein, $R_{14}$ and $R_{15}$ are independently selected from a lower alkyl, a lower haloalkyl or $R_{14}$ and $R_{15}$ together with the carbon to which they are attached form a cyclic haloalkyl group;

$A_1$—$B_1$ is —NHC(O)—, —OCH$_2$—, —SCH$_2$—NHCH$_2$, —CH=CH—, or —CH=CH—; and $Y_1$ is an aryl group; and $D_2$ is as defined herein.

Another embodiment of the present invention describes novel nitrosated and/or nitrosylated potassium channel activators of Formula (VI):

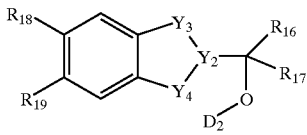

VI wherein, $R_{16}$ and $R_{17}$ are each independently a lower alkyl, a lower haloalkyl or $R_{16}$ and $R_{17}$ together with the carbon to which they are attached form a cyclic haloalkyl group;

$Y_3$ is an sp$^2$-hybridized atom and $Y_2$, $Y_3$ and $Y_4$ together with the carbon atoms to which they are attached form a 5- or 6-membered heterocyclic ring;

$R_{18}$ and $R_{19}$ are each independently a hydrogen, a nitro, a cyano, a halo, a haloalkyl, an alkylsulfonyl, or an aryl, with the proviso that either $R_{18}$ or $R_{19}$ must be a hydrogen but that both $R_{18}$ and $R_{19}$ cannot be a hydrogen; and $D_2$ is as defined herein.

Compounds of the present invention which have one or more asymmetric carbon atoms can exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof.

Another aspect of the present invention provides processes for making the novel compounds of the invention and to the intermediates useful in such processes. The compounds of the present invention of Formula (I), Formula (II) Formula (III), Formula (IV), Formula (V) and Formula (III) can be synthesized by one skilled in the art following the methods and examples described herein. Compounds of the invention can be synthesized as shown in FIGS. 1–16 in which A, B, $A_1$, $B_1$, D, $D_1$, $D_3$, E, G, Q, T, W, X, $R_1$, $R_2$, $R_3$, $R_4$, $R_5$, $R_6$, $R_7$, $R_8$, $R_{14}$, $R_{15}$, $R_{16}$, $R_{17}$, $R_{18}$, $R_{19}$, $R_e$, $R_f$, a, b, c, d, g, i, j, p, q, x, y and z are as defined herein or as depicted in the reaction schemes for Formulas (I), (II), (III), (IV), (V) and (VI); $P^1$ is an oxygen protecting group and $P^2$ is a sulfur protecting group. The reactions are performed in solvents appropriate to the reagents, and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is known in the art for protecting thiol and alcohol groups against undesirable reactions during a synthetic procedure and many such protecting groups are known, e.g., T. H. Greene and P. G. M. Wuts, *Protective Groups in Organic Synthesis*, John Wiley & Sons, New York (1991).

Nitroso compounds of Formula (I) where $R_1$ is as defined herein and a nitrite containing N-amide is representative of the (C(B)-T-D) group as defined herein can be prepared as outlined in FIG. 1. The acid group of structure 1 is converted to the amide of structure 2 wherein R is —$W_{a-1}$-$E_b$—(C(R$_e$)(R$_f$))$_p$-$E_c$-(C(R$_e$)(R$_f$))$_x$—$W_d$—(C(R$_e$)(R$_f$))$_y$—$W_i$-$E_j$-$W_g$—(C(R$_e$)(R$_f$))$_z$ by reaction with an appropriate protected alcohol containing amine, wherein $R_i$ and $P^1$ are as defined herein. Preferred methods for the preparation of amides are initially forming the mixed anhydride via reaction of the acid with a chloroformate, such as isobutylchloroformate, in the presence of a non-nucleophilic base, such as triethylamine, in an anhydrous inert solvent, such as dichloromethane, diethylether or THF. The mixed anhydride is then reacted with the monoprotected alcohol, preferably in the presence of a condensation catalyst, such as 4-dimethylamino pyridine (DMPA). Alternatively, the acid can first be converted to the acid chloride by treatment with oxalyl chloride in the presence of a catalytic amount of DMF. The acid chloride is then reacted with the protected alcohol containing amine, preferably in the presence of a condensation catalyst, such as 4-dimethylamino pyridine (DMAP), and a tertiary amine base, such as triethyl amine, to produce the amide. Alternatively, the acid and protected alcohol containing amine can be coupled to produce the amide by treatment with a dehydration agent, such as dicyclohexylcarbodiimide (DCC) or 1-(3-dimethylaminopropyl)-3-ethylcarbodiimide hydrochloride (EDC) with or without a condensation catalyst such as DMAP. Preferred protecting groups for the alcohol moiety are silyl ethers, such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent, such as thionyl chloride nitrite, thionyl dinitrite or nitrosium tetrafluoroborate, in a suitable anhydrous solvent, such as dichlormethane, THF, DMF or acetonitrile, with or without an amine base, such as pyridine or triethylamine, produces the compounds of structure IA.

Figure 2:
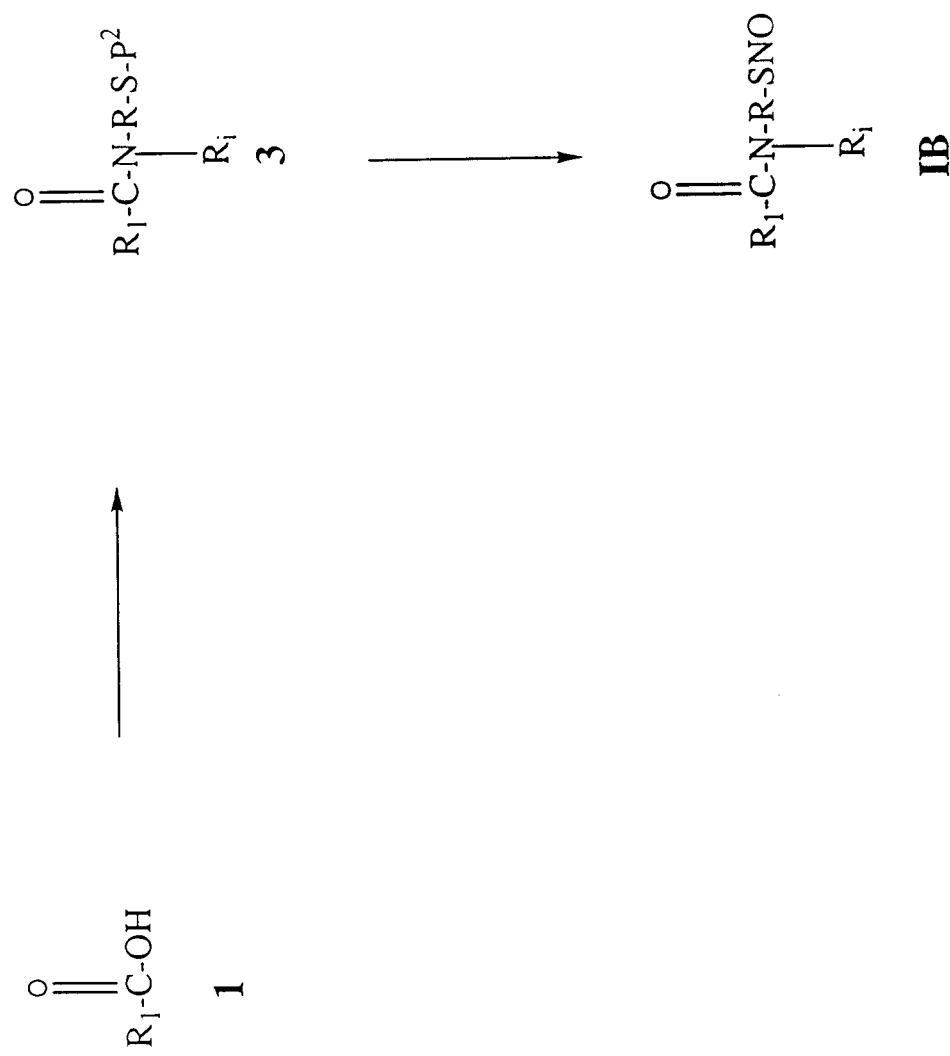
FIG. 2 is the synthetic scheme for the preparation of a nitrosothiol containing N-amide of Formula (I).

Nitroso compounds of Formula (I) wherein $R_1$ is as defined herein and a nitrosothiol containing amide is representative of the (C(B)-T-D) group as defined herein can be prepared as outlined in FIG. 2. The acid group of structure 1 is converted to the amide of structure 3 by reaction with an appropriate protected thiol containing amine wherein R, $R_i$ and $P^2$ are as defined herein. Preferred methods for the preparation of amides are initially forming the mixed anhydride via reaction of the acid with a chloroformate, such as isobutylchloroformate, in the presence of a non-nucleophilic base, such as triethylamine, in an anhydrous inert solvent, such as dichloromethane, diethylether or THF. The mixed anhydride is then reacted with the thiol protected amine, preferably in the presence of a condensation catalyst, such as 4-dimethylamino pyridine (DMAP). Alternatively, the acid can first be converted to the acid chloride by treatment with oxalyl chloride in the presence of a catalytic amount of DMF. The acid chloride is then reacted with the protected thiol containing amine, preferably in the presence of a condensation catalyst, such as 4-dimethylamino pyridine (DMAP), and a tertiary amine base, such as triethyl amine, to produce the amide. Alternatively, the acid and protected thiol containing amine can be coupled to produce the amide by treatment with a dehydration agent, such as dicyclohexylcarbodiimide (DCC) or 1-(3-dimethylaminopropyl)-3-ethylcarbodiimide hydrochloride (EDC) with or without a condensation catalyst such as DMAP. Preferred protecting groups for the thiol moiety are as a thioester, such as thioacetate or thiobenzoate, as a disulfide, as a thiocarbamate, such as N-methoxymethyl thiocarbamate, or as a thioether, such as paramethoxybenzyl thioether, a 2,4,6-trimethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate or strong acids such as trifluoroacetic or hydrochloric acid and heat are used to remove a paramethoxybenzyl thioether, a 2,4,6-trimethoxybenzyl thioether a tetrahydropyranyl thioether or a S-triphenylmethyl thioether group) followed by reaction with a suitable nitrosylating agent, such as thionyl chloride nitrite, thionyl dinitrite, a lower alkyl nitrite, such as tert-butyl nitrite, or nitrosium tetrafluoroborate, in a suitable anhydrous solvent, such as methylene chloride, THF, DMF or acetonitrile, with or without an amine base, such as pyridine or triethylamine, produces the compounds of structure IB. Alternatively, a stoichiometric quantity of sodium nitrite in alcoholic or aqueous acid produces the compounds of structure IB.

Figure 3:
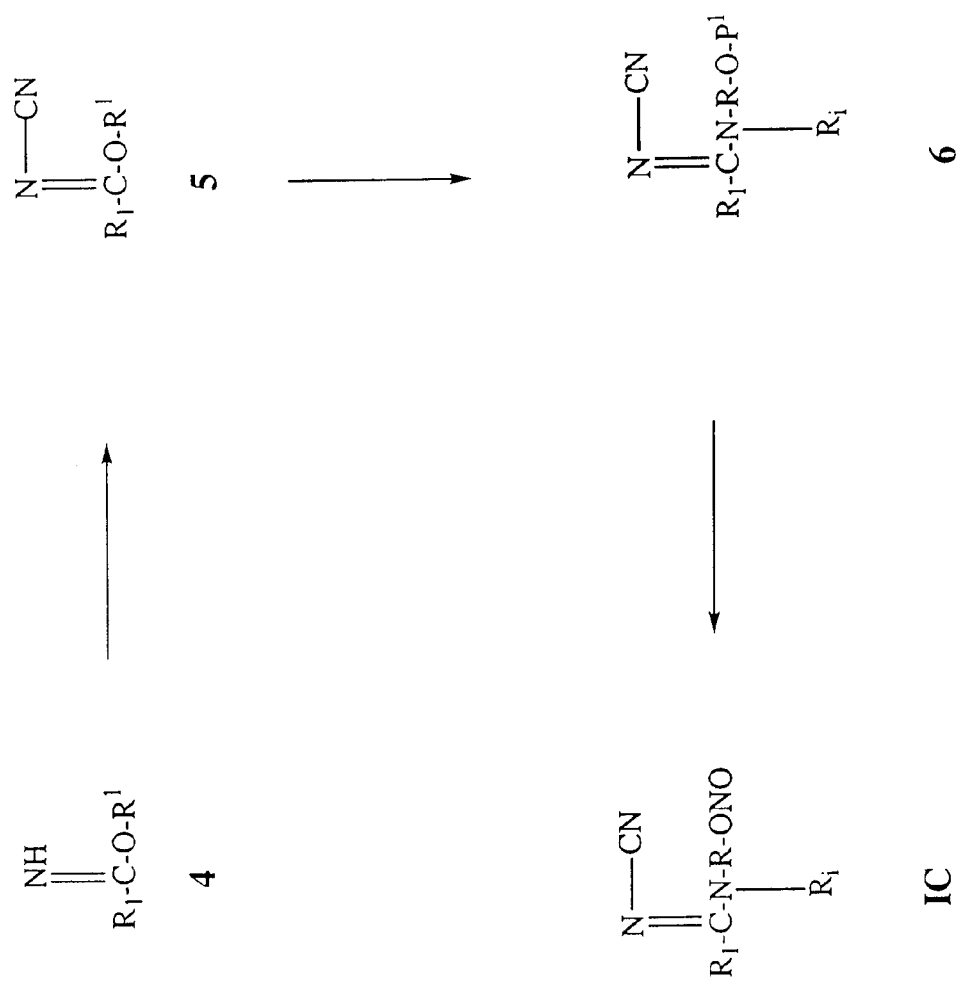
FIG. 3 is the synthetic scheme for the preparation of a nitrite containing N-cyano-N'substituted-carboximidamide of Formula (I).

Nitroso compounds of Formula (I) wherein $R_1$ is as defined herein and a nitrite containing N-cyano-N'substituted-carboximidamide is representative of the (C(B)-T-D) group as defined herein can be prepared as outlined in FIG. 3. The imidate of structure 4 wherein R' is an alkyl or cycloalkyl group is converted to the N-cyano-carboximidate of structure 5 by reaction with cyanamide in buffered solution between pH 5.0–6.0. The compound of structure 5 is converted to the compound of structure 6 by reaction with an appropriate protected alcohol containing amine wherein R, $R_i$ and $P^1$ are as defined herein in an appropriate solvent such as methanol, ethanol, methylene chloride, THF, chloroform, dioxane or carbon tetra-chloride. Preferred protecting groups for the alcohol moiety are silyl ethers, such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent, such as thionyl chloride nitrite, thionyl dinitrite or nitrosium tetrafluoroborate, in a suitable anhydrous solvent, such as dichlormethane, THF, DMF or acetonitrile, with or without an amine base, such as pyridine or triethylamine, produces the compounds of structure IC.

Figure 4:
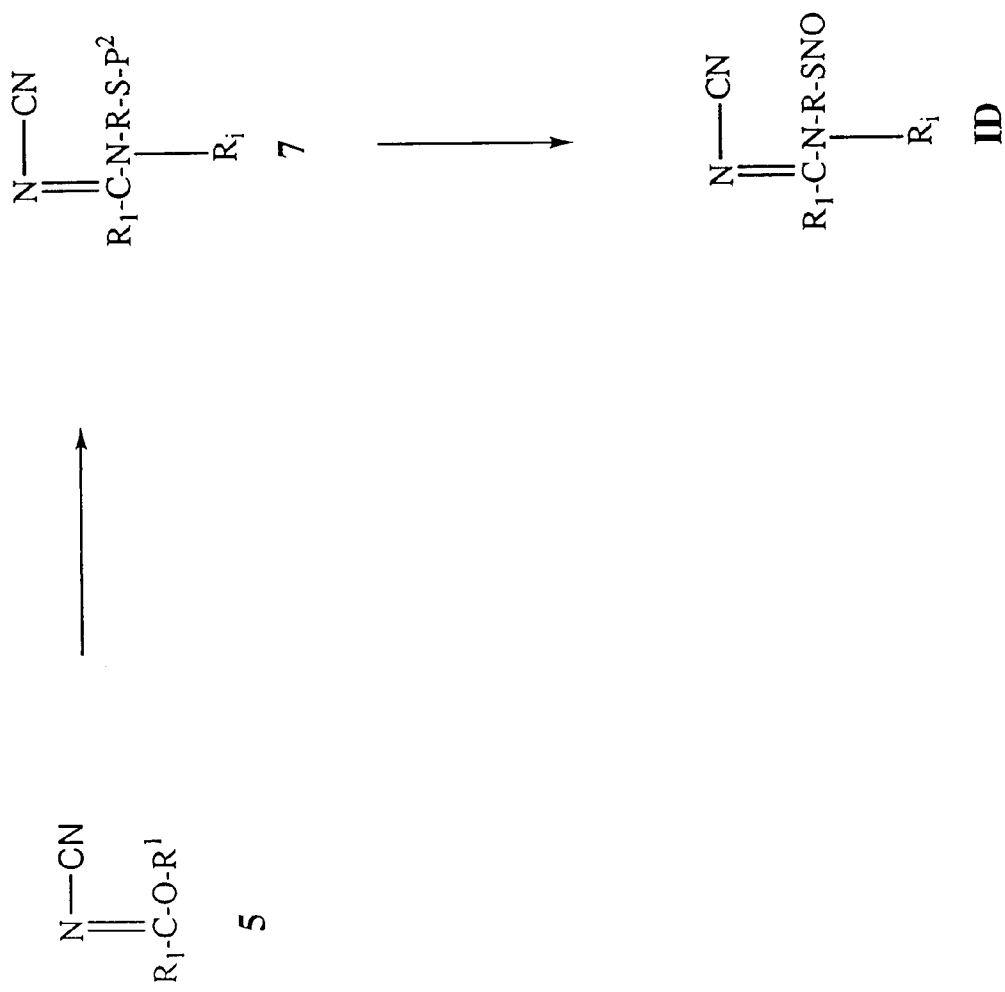
FIG. 4 is the synthetic scheme for the preparation of a nitrosothiol containing N-cyano-N'substituted-carboximidamide of Formula (I).

Nitroso compounds of Formula (I) wherein $R_1$ is as defined herein and a nitrosothiol containing N-cyano-N'substituted-carboximidamide is representative of the (C(B)-T-D) group as defined herein can be prepared as outlined in FIG. 4. The compound of structure 5 wherein R' is as defined herein is converted to the compound of structure 7 by reaction with an appropriate protected thiol containing amine wherein R, $R_i$ and $P^2$ are as defined herein in an appropriate solvent such as methanol, ethanol, methylene chloride, THF, chloroform, dioxane or carbon tetra-chloride. Preferred protecting groups for the thiol moiety are as a disulfide, as a thiocarbamate, such as N-methoxymethyl thiocarbamate, or as a thioether, such as paramethoxybenzyl thioether, a 2,4,6-trimethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while mercuric trifluoroacetate, silver nitrate or strong acids such as trifluoroacetic or hydrochloric acid and heat are used to remove a paramethoxybenzyl thioether, a 2,4,6-trimethoxybenzyl thioether a tetrahydropyranyl thioether or a S-triphenylmethyl thioether group) followed by reaction with a suitable nitrosylating agent, such as thionyl chloride nitrite, thionyl dinitrite, a lower alkyl nitrite, such as tert-butyl nitrite, or nitrosium tetrafluoroborate, in a suitable anhydrous solvent, such as methylene chloride, THF, DMF or acetonitrile, with or without an amine base, such as pyridine or triethylamine, produces the compounds of structure ID. Alternatively, a stoichiometric quantity of sodium nitrite in alcoholic or aqueous acid produces the compounds of structure ID.

Figure 5:
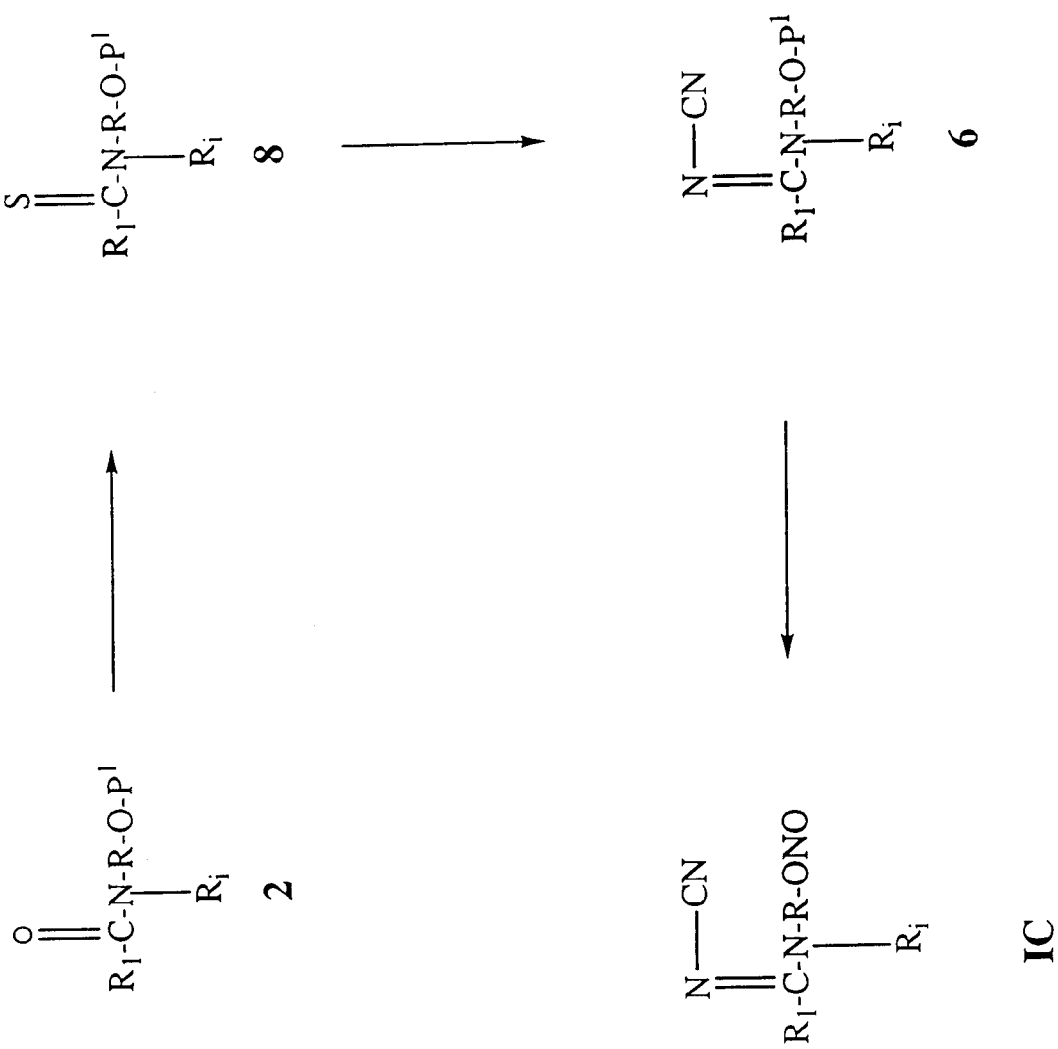
FIG. 5 is the synthetic scheme for the preparation of a nitrite containing N-cyano-N'substituted-carboximidamide of Formula (I).

Nitroso compounds of Formula (I) wherein $R_1$ is as defined herein and a nitrite containing N-cyano-N'substituted-carboximidamide is representative of the (C(B)-T-D) group as defined herein can be prepared as outlined in FIG. 5. The amide of formula 2 wherein R, $R_i$ and $P^1$ are as defined herein is converted to the compound of structure 8 by reaction with $P_2S_5$ or Lawesson's reagent under standard conditions (cf. *Tetrahedron*, 35, 2433 (1979)). The compound of structure 8 is converted to the compound of structure 6 by reaction with excess cyanamide in the presence of phosphorus oxychloride, phosphorus pentoxide, phosphorus pentachloride, thionyl chloride, or sulfuryl chloride in the presence of a tertiary amine such as triethylamine or diisopropylethyl amine in an inert solvent such as acetonitrile, benzene, toluene, methylene chloride, chloroform, carbon tetrachloride, tetrahydrofuran, DMF and the like at a temperature ranging from room temperature up to the atmospheric boiling temperature of the solvent. The compound of structure 6 is converted into the compound of structure IC as described herein.

Figure 6:
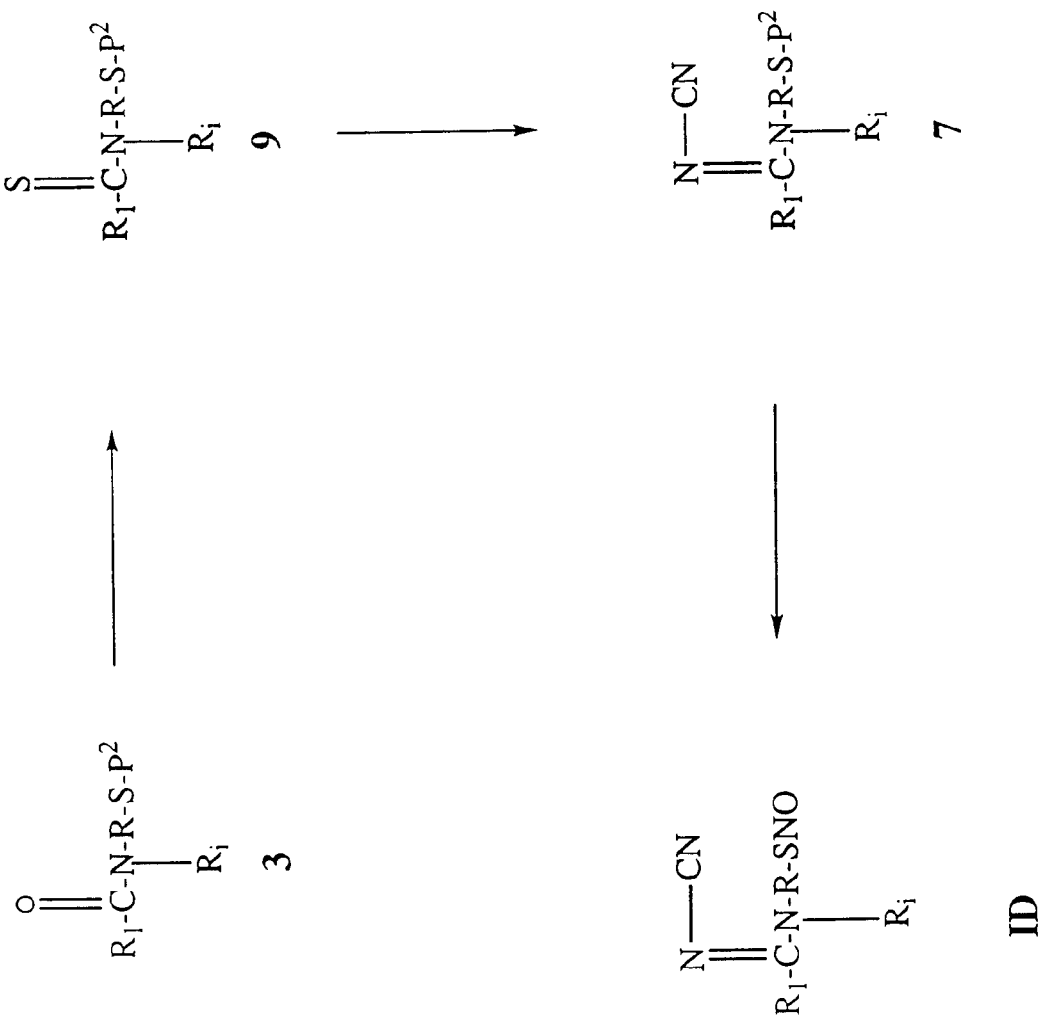
FIG. 6 is the synthetic scheme for the preparation of a nitrosothiol containing N-cyano-N'substituted-carboximidamide of Formula (I).

Nitroso compounds of Formula (I) wherein $R_1$ is as defined herein and a nitrite containing N-cyano-N'substituted-carboximidamide is representative of the (C(B)-T-D) group as defined herein can be prepared as outlined in FIG. 6. The amide of structure 3 wherein R, $R_i$ and $P^2$ are as defined herein is converted to the compound of structure 9 by reaction with $P_2S_5$ or Lawesson's reagent as described herein. The compound of structure 9 is converted to the compound of structure 7 by reaction with excess cyanamide in the presence of phosphorus oxychloride, phosphorus pentoxide, phosphorus pentachloride, thionyl chloride, or sulfuryl chloride in the presence of a tertiary amine such as triethylamine or diisopropylethyl amine in an inert solvent such as acetonitrile, benzene, toluene, methylene chloride, chloroform, carbon tetrachloride, tetrahydrofuran, DMF and the like at a temperature ranging from room temperature up to the atmospheric boiling temperature of the solvent. The compound of structure 7 is converted into the compound of structure ID as described herein.

Figure 7:
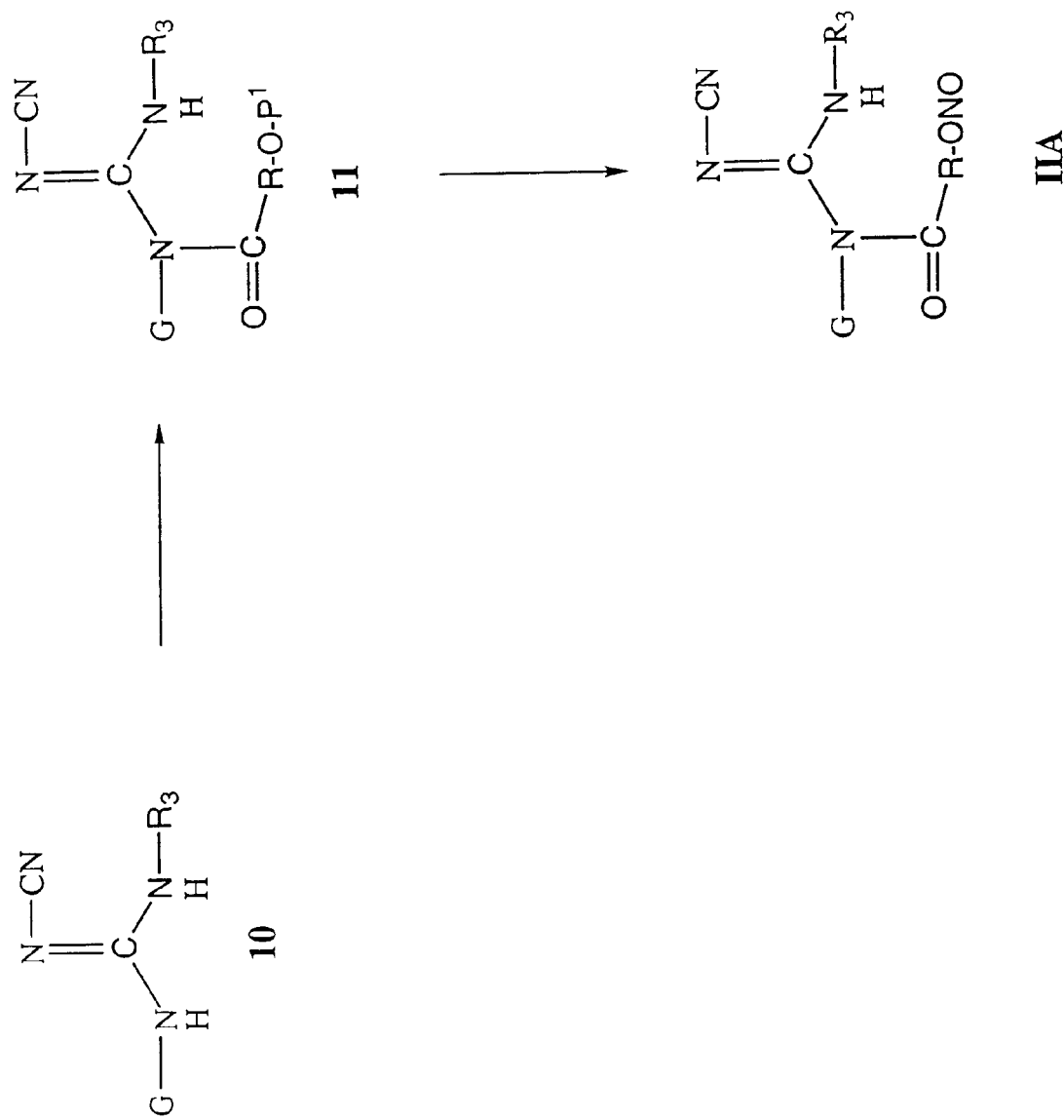
FIG. 7 is the synthetic scheme for the preparation of a nitrite containing acyl group of Formula (II).

Nitroso compounds of Formula (II) wherein G and $R_3$ are as defined herein and a nitrite containing acyl group is representative of the $D_3$ group as defined herein can be prepared as outlined in FIG. 7. The substituted cyano guanidine of structure 10 is converted to the compound of the structure 11 wherein R is as defined herein by reaction with an appropriate protected alcohol containing activated acylating agent wherein $P^1$ is as defined herein. Preferred methods for the formation of acylated substituted cyanoguanidines is reacting the substituted cyanoguanidine with the preformed acid chloride or symmetrical anhydride of the protected alcohol containing acid or condensing the substituted cyanoguanidine and protected alcohol containing acid in the presence of a dehydrating agent such as dicyclohexylcarbo-diimide (DCC) or 1-ethyl-3 (3-dimethylaminopropyl) carbodiimide hydrochloride (EDAC HCl) with a catalyst such as 4-dimethylaminopyridine (DMAP) or 1-hydroxy-benzotriazole (HOBt). Preferred protecting groups for the alcohol moiety are silyl ethers such as a trimethylsilyl or tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the structure IIA.

Figure 8:
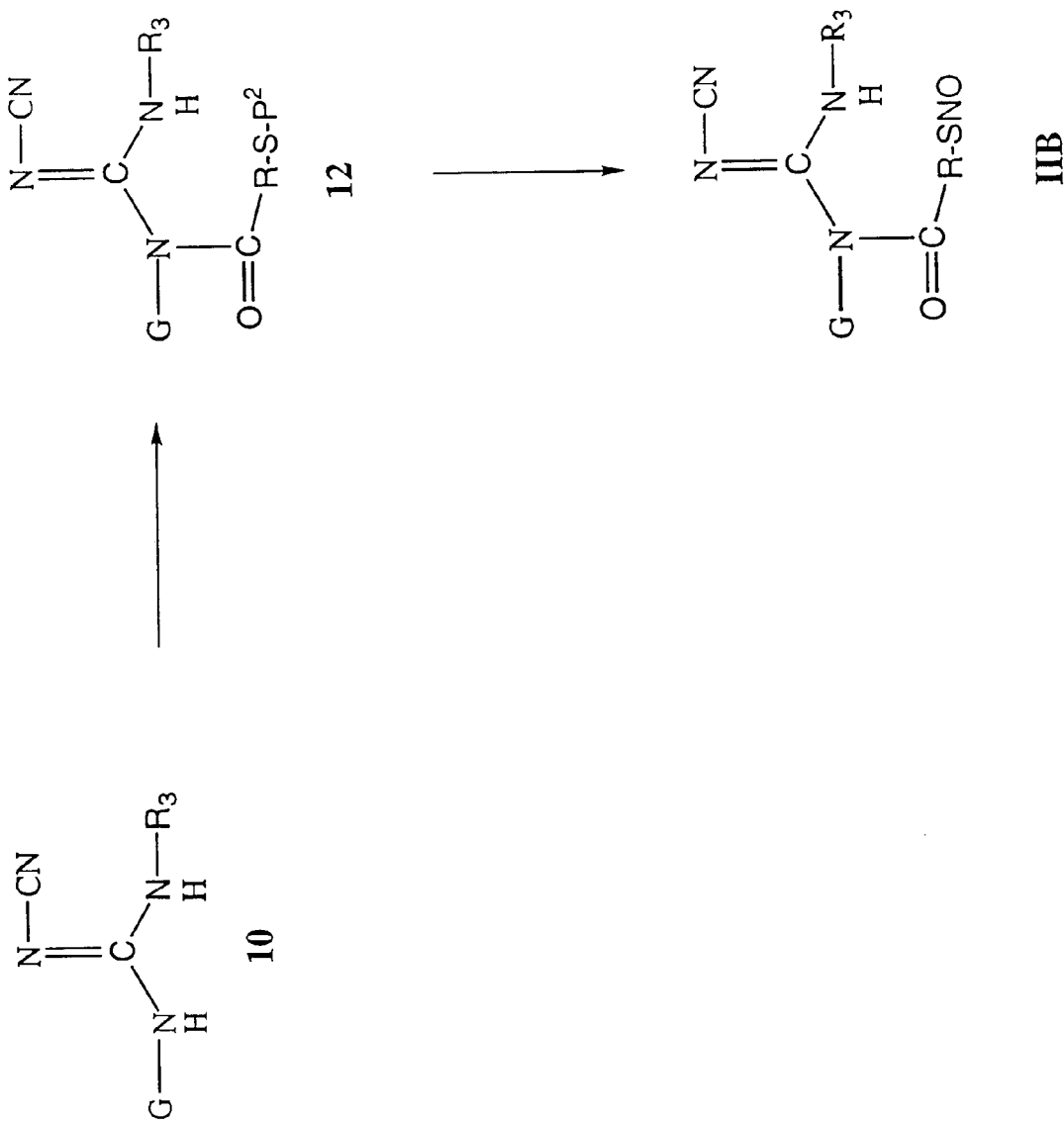
FIG. 8 is the synthetic scheme for the preparation of a nitrosothiol containing acyl group of Formula (II).

Nitroso compounds of Formula (II) wherein G and $R_3$ are as defined herein and a nitrosothiol containing acyl group is representative of the $D_3$ group as defined herein can be prepared as outlined in FIG. 8. The substituted cyano guanidine of structure 10 is converted to the compound of the structure 12 wherein R is as defined herein by reaction with an appropriate protected thiol containing activated acylating agent wherein $P^2$ is as defined herein. Preferred methods for the formation of acylated substituted cyanoguanidines are reacting the substituted cyanoguanidine with the preformed acid chloride or symmetrical anhydride of the protected thiol containing acid or condensing the substituted cyanoguanidine and protected thiol containing acid in the presence of a dehydrating agent such as dicyclohexylcarbodiimide (DCC) or 1-ethyl-3 (3-dimethylaminopropyl) carbodiimide hydrochloride (EDAC HCl) with a catalyst such as 4-dimethylaminopyridine (DMAP) or 1-hydroxybenzotriazole (HOBt). Preferred protecting groups for the thiol moiety are as a thioester, such as thioacetate or thiobenzoate, as a disulfide, as a thiocarbamate, such as N-methoxy-methyl thiocarbamate, or as a thioether, such as paramethoxybenzyl thioether, a 2,4,6-trimethoxybenzyl thioether, a tetrahydropyranyl thioether, or a S-triphenylmethyl thioether. Deprotection of the thiol moiety (zinc in dilute aqueous acid, triphenyl-phosphine in water and sodium borohydride are preferred methods for reducing disulfide groups while aqueous base is typically used to hydrolyze thioesters and N-methoxymethyl thiocarbamates and mercuric trifluoroacetate, silver nitrate or strong acids such as trifluoroacetic or hydrochloric acid and heat are used to remove a paramethoxybenzyl thioether, a 2,4,6-trimethoxybenzyl thioether a tetrahydropyranyl thioether or a S-triphenylmethyl thioether group) followed by reaction with a suitable nitrosylating agent, such as thionyl chloride nitrite, thionyl dinitrite, a lower alkyl nitrite, such as tert-butyl nitrite, or nitrosium tetrafluoroborate, in a suitable anhydrous solvent, such as methylene chloride, THF, DMF or acetonitrile, with or without an amine base, such as pyridine or triethylamine, produces the compounds of structure IIB. Alternatively, a stoichiometric quantity of sodium nitrite in alcoholic or aqueous acid produces the compounds of structure IIB.

Figure 9:
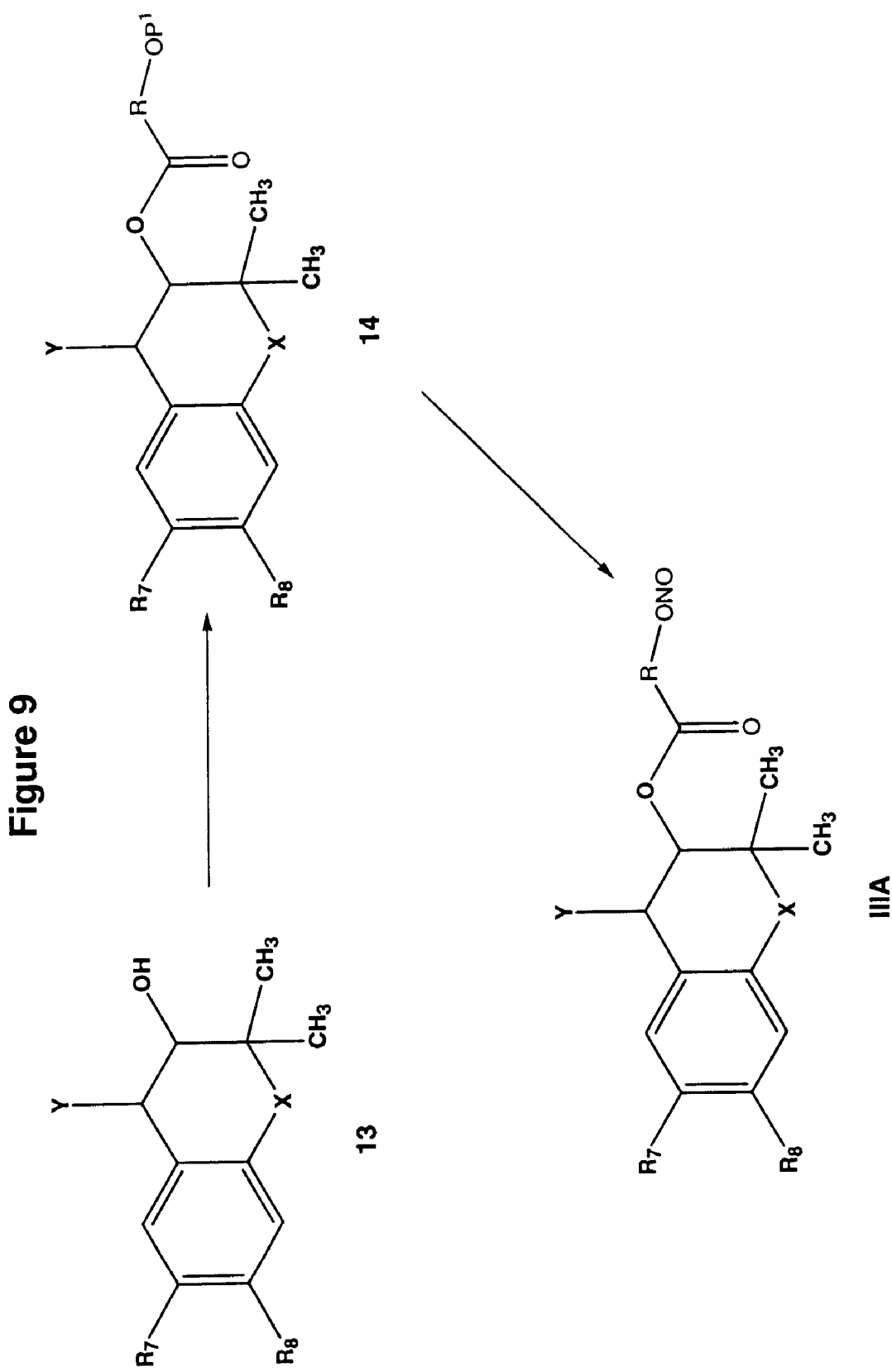
FIG. 9 is the synthetic scheme for the preparation of a nitrite containing acyl group of Formula (III).

Nitroso compounds of Formula (III) wherein X, Y, $R_7$ and $R_8$ are defined as herein and a nitrite containing acyl group is representative of the $D_2$ group as defined herein can be prepared as outlined in FIG. 9. The alcohol of structure 13 is converted to the acyl derivative of the structure 14 wherein R is as defined herein by reaction with an appropriate protected alcohol containing activated acylating agent wherein $P^1$ is as defined herein. Preferred methods for the formation of esters is reacting the alcohol with the preformed acid chloride or symmetrical anhydride of the protected alcohol containing acid or condensing the alcohol and protected alcohol containing acid in the presence of a dehydrating agent such as dicyclohexylcarbodiimide (DCC) or 1-ethyl-3 (3-dimethyl-aminopropyl) carbodiimide hydrochloride (EDAC HCl) with a catalyst such as 4-dimethylaminopyridine (DMAP) or 1-hydroxybenzotriazole (HOBt). Preferred protecting groups for the alcohol moiety are silyl ethers such as a trimethylsilyl or tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloro-methane, THF, DMF, or acetonitrile with or without an amine base such as pyridine or triethylamine affords the compound of the structure IIIA.

Figure 10:
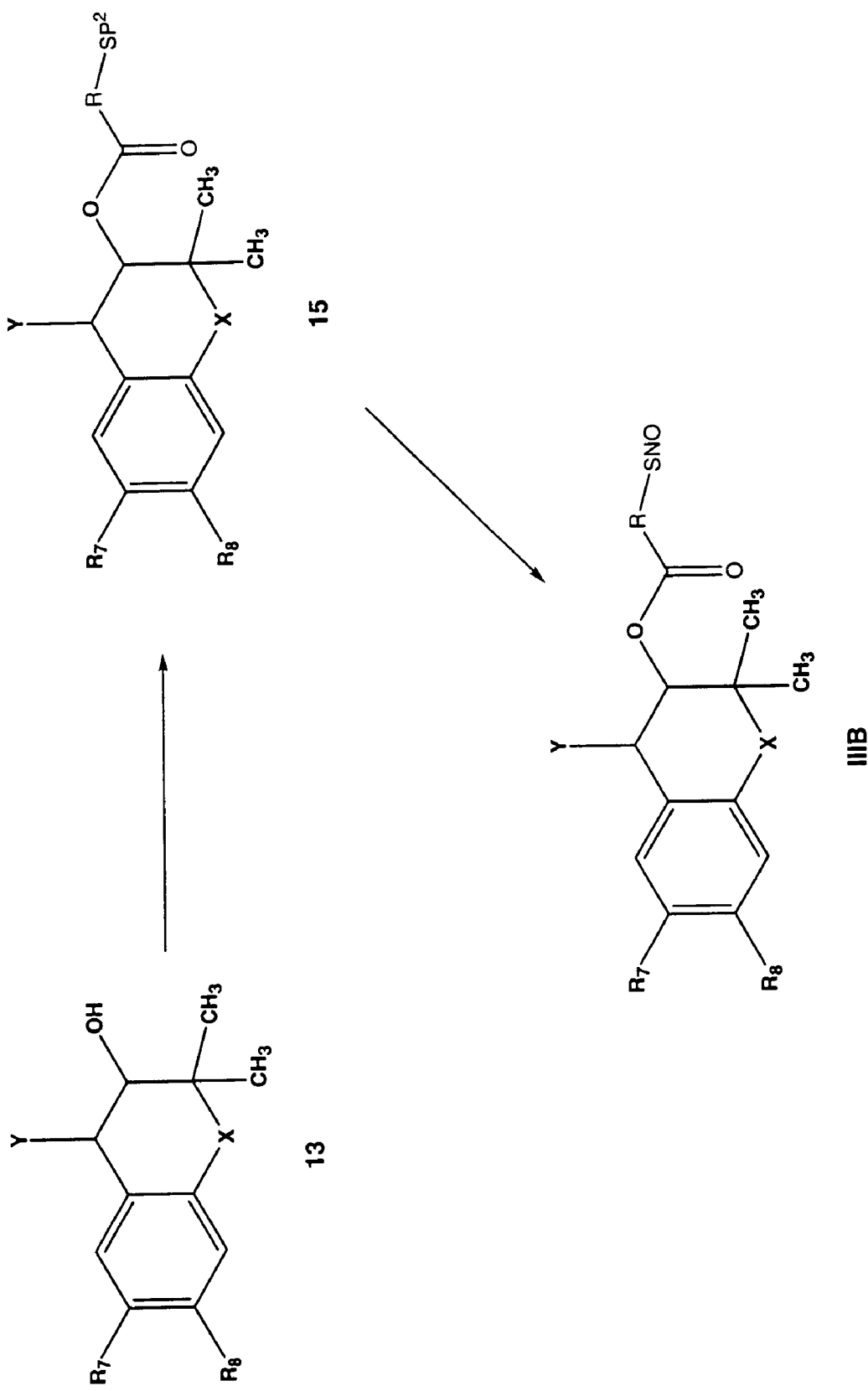
FIG. 10 is the synthetic scheme for the preparation of a nitrosothiol containing acyl group of Formula (III).

Nitroso compounds of Formula (III) wherein X, Y, $R_7$ and $R_8$ are defined as herein and a nitrosothiol containing acyl group is representative of the $D_2$ group as defined herein can be prepared as outlined in FIG. 10. The alcohol of structure 13 is converted to the acyl derivative of the structure 15 wherein R is as defined herein by reaction with an appropriate protected thiol containing activated acylating agent wherein $P^2$ is as defined herein. Preferred methods for the formation of esters are reacting the alcohol with the preformed acid chloride or symmetrical anhydride of the protected thiol containing acid or condensing the alcohol and protected thiol containing acid in the presence of a dehydrating agent such as dicyclohexylcarbodiimide (DCC) or 1-ethyl-3 (3-dimethyl-aminopropyl) carbodiimide hydrochloride (EDAC HCl) with a catalyst such as 4-dimethylaminopyridine (DMAP) or 1-hydroxybenzotriazole (HOBt). Preferred protecting groups for the thiol moiety are as a thioester, such as thioacetate or thiobenzoate, as a disulfide, as a thiocarbamate, such as N-methoxymethyl thiocarbamate, or as a thioether, such as paramethoxybenzyl thioether, a 2,4,6-trimethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate or strong acids such as trifluoroacetic or hydrochloric acid and heat are used to remove a paramethoxybenzyl thioether, a 2,4,6-trimethoxybenzyl thioether a tetrahydropyranyl thioether or a S-triphenylmethyl thioether group) followed by reaction with a suitable nitrosylating agent, such as thionyl chloride nitrite, thionyl dinitrite, a lower alkyl nitrite, such as tert-butyl nitrite, or nitrosium tetrafluoroborate, in a suitable anhydrous solvent, such as methylene chloride, THF, DMF or acetonitrile, with or without an amine base, such as pyridine or triethylamine, produces the compounds of structure IIIB. Alternatively, a stoichiometric quantity of sodium nitrite in alcoholic or aqueous acid produces the compounds of structure IIIB.

Figure 11:
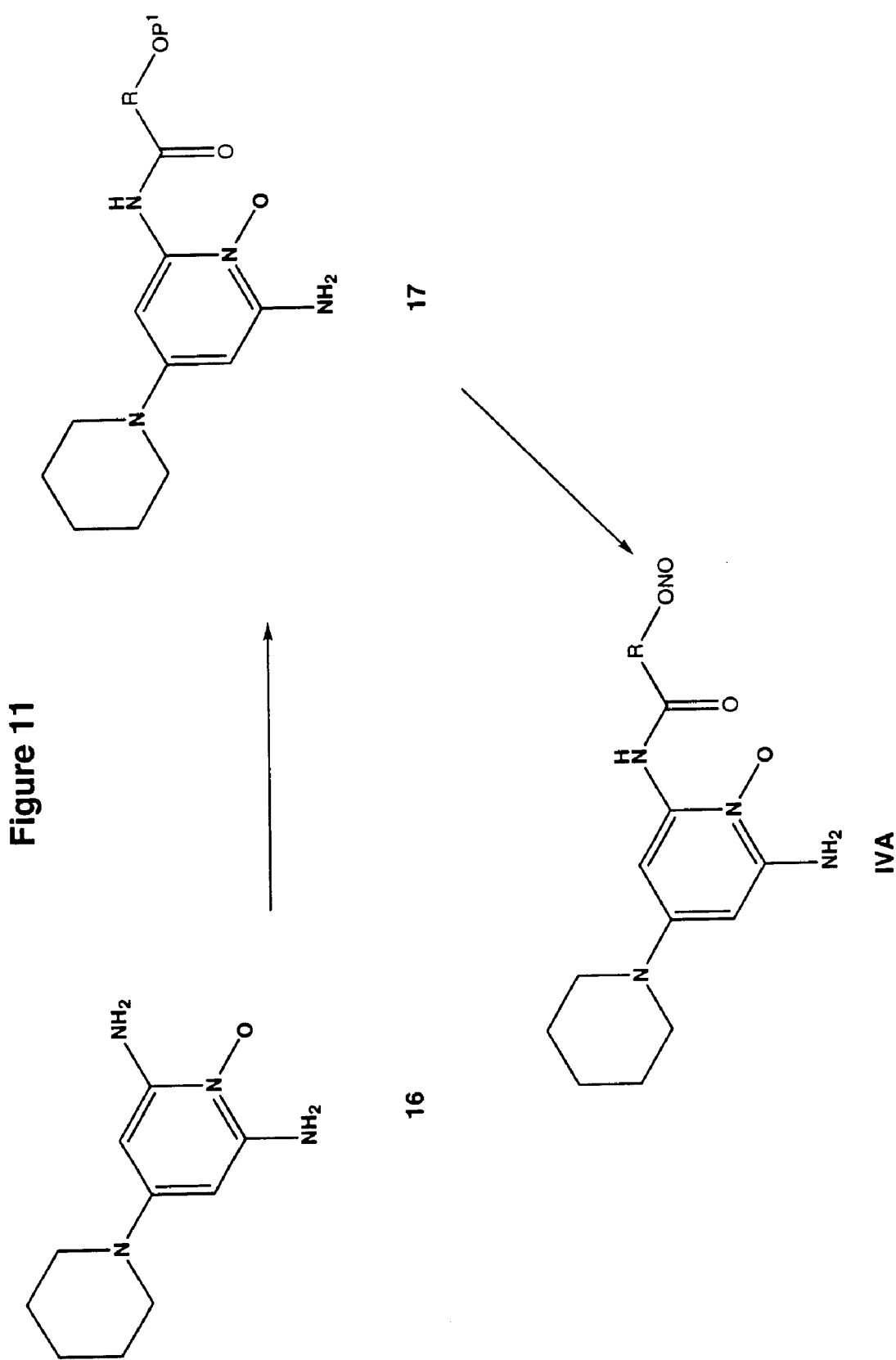
FIG. 11 is the synthetic scheme for the preparation of a nitrite containing acyl group of Formula (IV).

Nitroso compounds of Formula (IV) wherein a nitrite containing acyl group is representative of the $D_3$ group as defined herein can be prepared as outlined in FIG. 11. The amine of structure 16 is converted to the acyl derivative of the structure 17 wherein R is as defined herein by reaction with an appropriate protected alcohol containing activated acylating agent wherein $P^1$ is as defined herein. Preferred methods for the formation of amides is reacting the amine with the preformed acid chloride or symmetrical anhydride of the protected alcohol containing acid or condensing the alcohol and protected alcohol containing acid in the presence of a dehydrating agent such as dicyclohexylcarbodiimide (DCC) or 1-ethyl-3 (3-dimethyl-aminopropyl) carbodiimide hydrochloride (EDAC HCl) with a catalyst such as 4-dimethylaminopyridine (DMAP) or 1-hydroxybenzotriazole (HOBt). Preferred protecting groups for the alcohol moiety are silyl ethers such as a trimethylsilyl or tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloro-methane, THF, DMF, or acetonitrile with or without an amine base such as pyridine or triethylamine affords the compound of the structure IVA.

Figure 12:
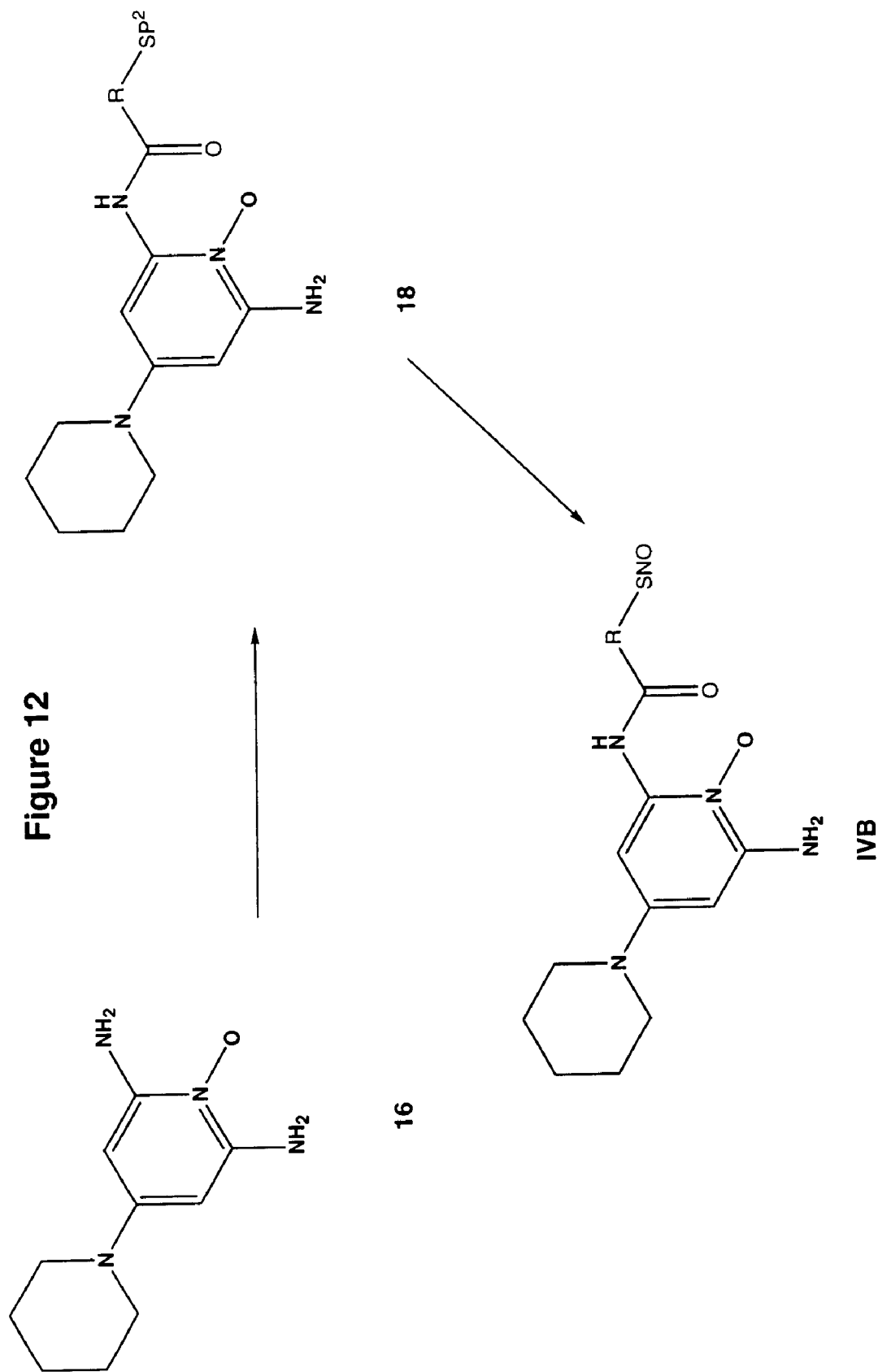
FIG. 12 is the synthetic scheme for the preparation of a nitrosothiol containing acyl group of Formula (IV).

Nitroso compounds of Formula (IV) where a nitrosothiol containing acyl group is representative of the $D_3$ group as defined herein can be prepared as outlined in FIG. 12. The amine of structure 16 is converted to the acyl derivative of the structure 18 wherein R is as defined herein by reaction with an appropriate protected thiol containing activated acylating agent wherein $P^2$ is as defined herein. Preferred methods for the formation of amides are reacting the alcohol with the preformed acid chloride or symmetrical anhydride of the protected thiol containing acid or condensing the alcohol and protected thiol containing acid in the presence of a dehydrating agent such as dicyclohexylcarbodiimide (DCC) or 1-ethyl-3 (3-dimethylaminopropyl) carbodiimide hydrochloride (EDAC HCl) with a catalyst such as 4-dimethylaminopyridine (DMAP) or 1-hydroxybenzotriazole (HOBt). Preferred protecting groups for the thiol moiety are as a thioester, such as thioacetate or thiobenzoate, as a disulfide, as a thiocarbamate, such as N-methoxymethyl thiocarbamate, or as a thioether, such as paramethoxybenzyl thioether, a 2,4,6-trimethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate or strong acids such as trifluoroacetic or hydrochloric acid and heat are used to remove a paramethoxybenzyl thioether, a 2,4,6-trimethoxybenzyl thioether a tetrahydropyranyl thioether or a S-triphenylmethyl thioether group) followed by reaction with a suitable nitrosylating agent, such as thionyl chloride nitrite, thionyl dinitrite, a lower alkyl nitrite, such as tert-butyl nitrite, or nitrosium tetrafluoroborate, in a suitable anhydrous solvent, such as methylene chloride, THF, DMF or acetonitrile, with or without an amine base, such as pyridine or triethylamine, produces the compounds of structure IVB. Alternatively, a stoichiometric quantity of sodium nitrite in alcoholic or aqueous acid produces the compounds of structure IVB.

Figure 13:
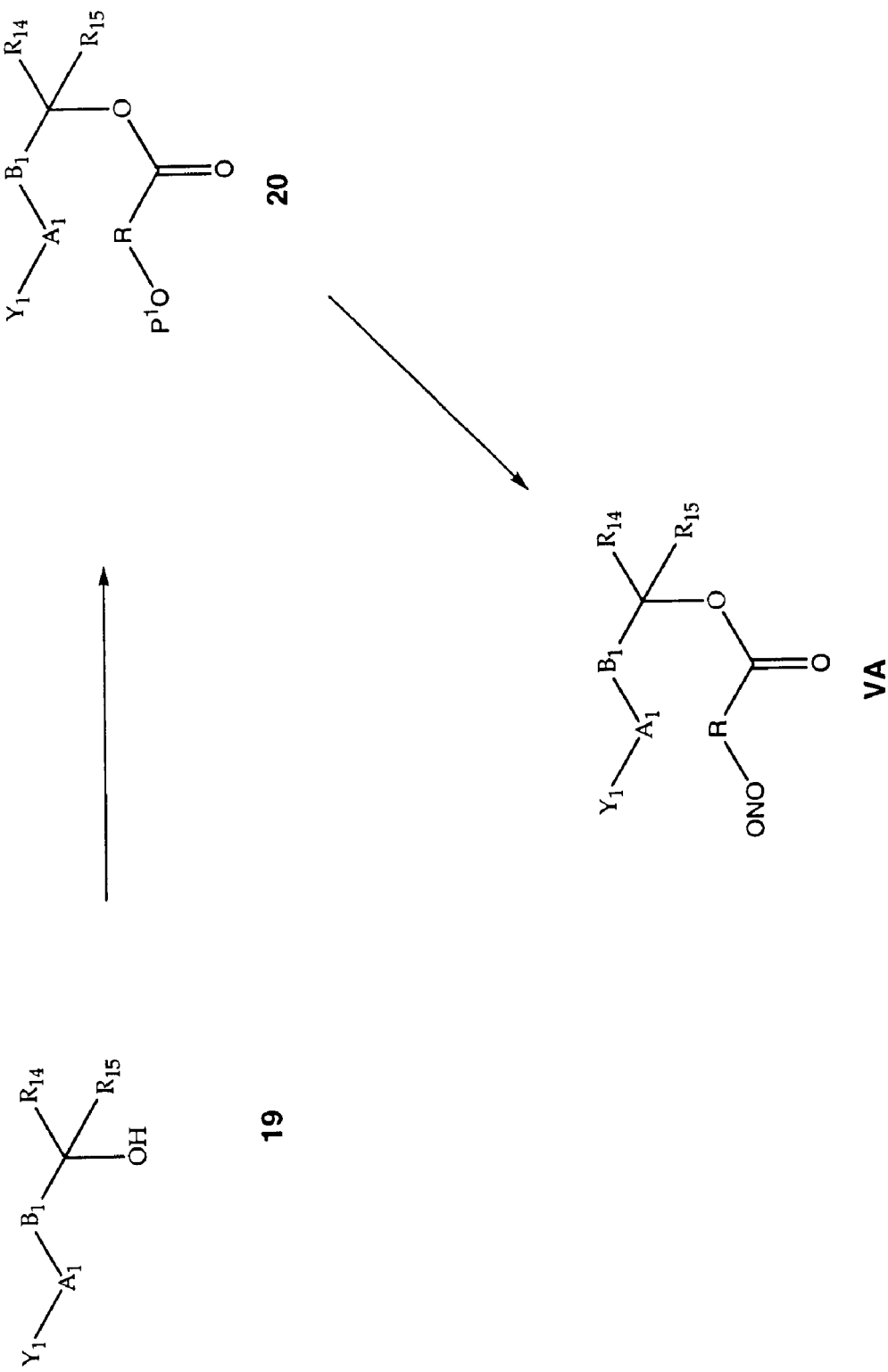
FIG. 13 is the synthetic scheme for the preparation of a nitrite containing acyl group of Formula (V).

Nitroso compounds of Formula (V) wherein $A_1$, $B_1$, $Y_1$, $R_{14}$ and $R_{15}$ are defined as herein and a nitrite containing acyl group is representative of the $D_2$ group as defined herein can be prepared as outlined in FIG. 13. The alcohol of structure 19 is converted to the acyl derivative of the structure 20 wherein R is as defined herein by reaction with an appropriate protected alcohol containing activated acylating agent wherein $P^1$ is as defined herein. Preferred methods for the formation of esters is reacting the alcohol with the preformed acid chloride or symmetrical anhydride of the protected alcohol containing acid or condensing the alcohol and protected alcohol containing acid in the presence of a dehydrating agent such as dicyclohexylcarbodiimide (DCC) or 1-ethyl-3 (3-dimethyl-aminopropyl) carbodiimide hydrochloride (EDAC HCl) with a catalyst such as 4-dimethylaminopyridine (DMAP) or 1-hydroxybenzotriazole (HOBt). Preferred protecting groups for the alcohol moiety are silyl ethers such as a trimethylsilyl or tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloro-methane, THF, DMF, or acetonitrile with or without an amine base such as pyridine or triethylamine affords the compound of the structure VA.

Figure 14:
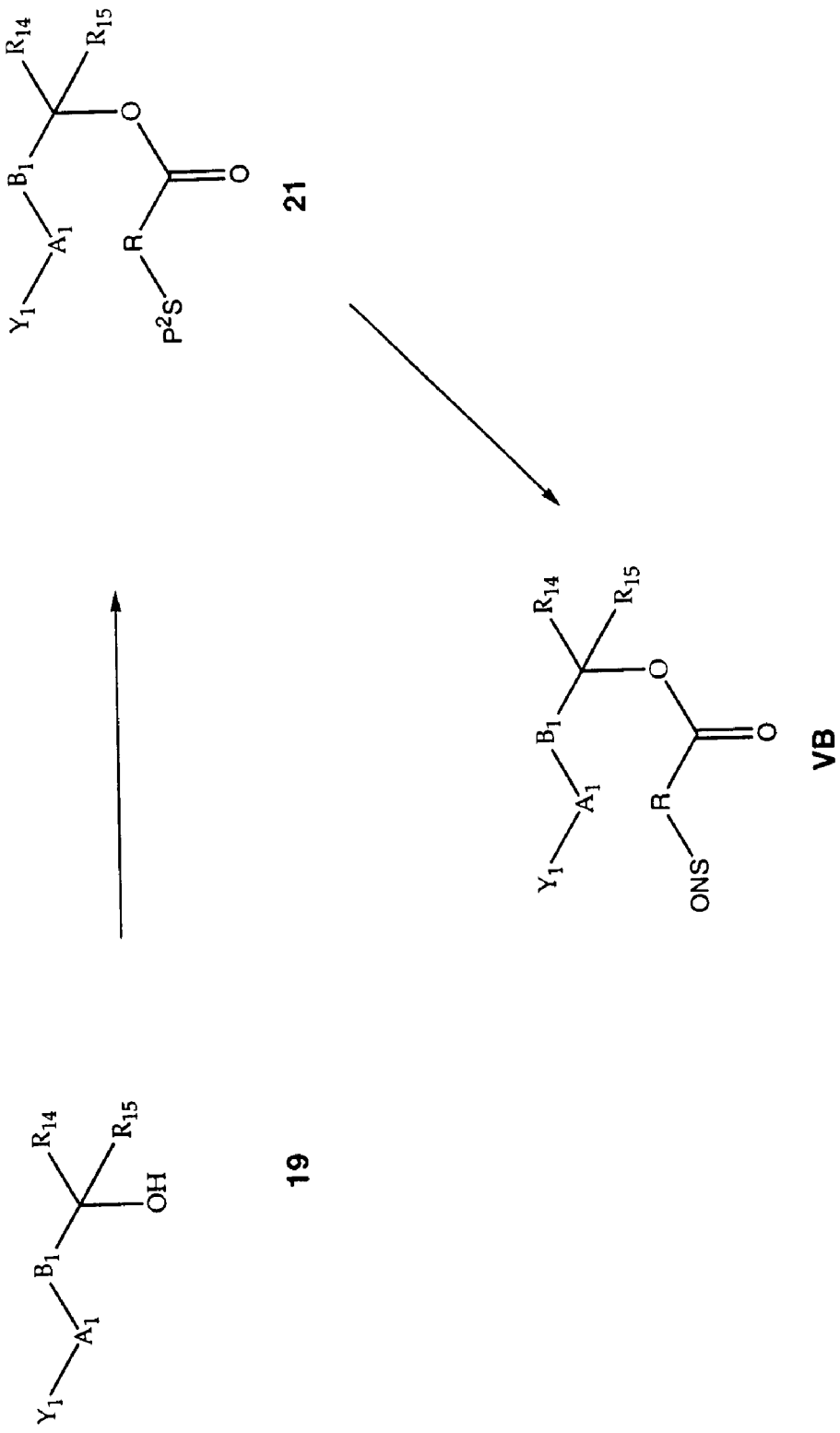
FIG. 14 is the synthetic scheme for the preparation of a nitrosothiol containing acyl group of Formula (V).

Nitroso compounds of Formula (V) wherein A, B, $Y_1$, $R_{14}$ and $R_{15}$ are defined as herein and a nitrosothiol containing acyl group is representative of the $D_2$ group as defined herein can be prepared as outlined in FIG. 14. The alcohol of structure 19 is converted to the acyl derivative of the structure 21 wherein R is as defined herein by reaction with an appropriate protected thiol containing activated acylating agent wherein $P^2$ is as defined herein. Preferred methods for the formation of esters are reacting the alcohol with the preformed acid chloride or symmetrical anhydride of the protected thiol containing acid or condensing the alcohol and protected thiol containing acid in the presence of a dehydrating agent such as dicyclohexylcarbodiimide (DCC) or 1-ethyl-3 (3-dimethyl-aminopropyl) carbodiimide hydrochloride (EDAC HCl) with a catalyst such as 4-dimethylaminopyridine (DMAP) or 1-hydroxybenzotriazole (HOBt). Preferred protecting groups for the thiol moiety are as a thioester, such as thioacetate or thiobenzoate, as a disulfide, as a thiocarbamate, such as N-methoxymethyl thiocarbamate, or as a thioether, such as paramethoxybenzyl thioether, a 2,4,6-trimethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate or strong acids such as trifluoroacetic or hydrochloric acid and heat are used to remove a paramethoxybenzyl thioether, a 2,4,6-trimethoxybenzyl thioether a tetrahydropyranyl thioether or a S-triphenylmethyl thioether group) followed by reaction with a suitable nitrosylating agent, such as thionyl chloride nitrite, thionyl dinitrite, a lower alkyl nitrite, such as tert-butyl nitrite, or nitrosium tetrafluoroborate, in a suitable anhydrous solvent, such as methylene chloride, THF, DMF or acetonitrile, with or without an amine base, such as pyridine or triethylamine, produces the compounds of structure VB. Alternatively, a stoichiometric quantity of sodium nitrite in alcoholic or aqueous acid produces the compounds of structure VB.

Figure 15:
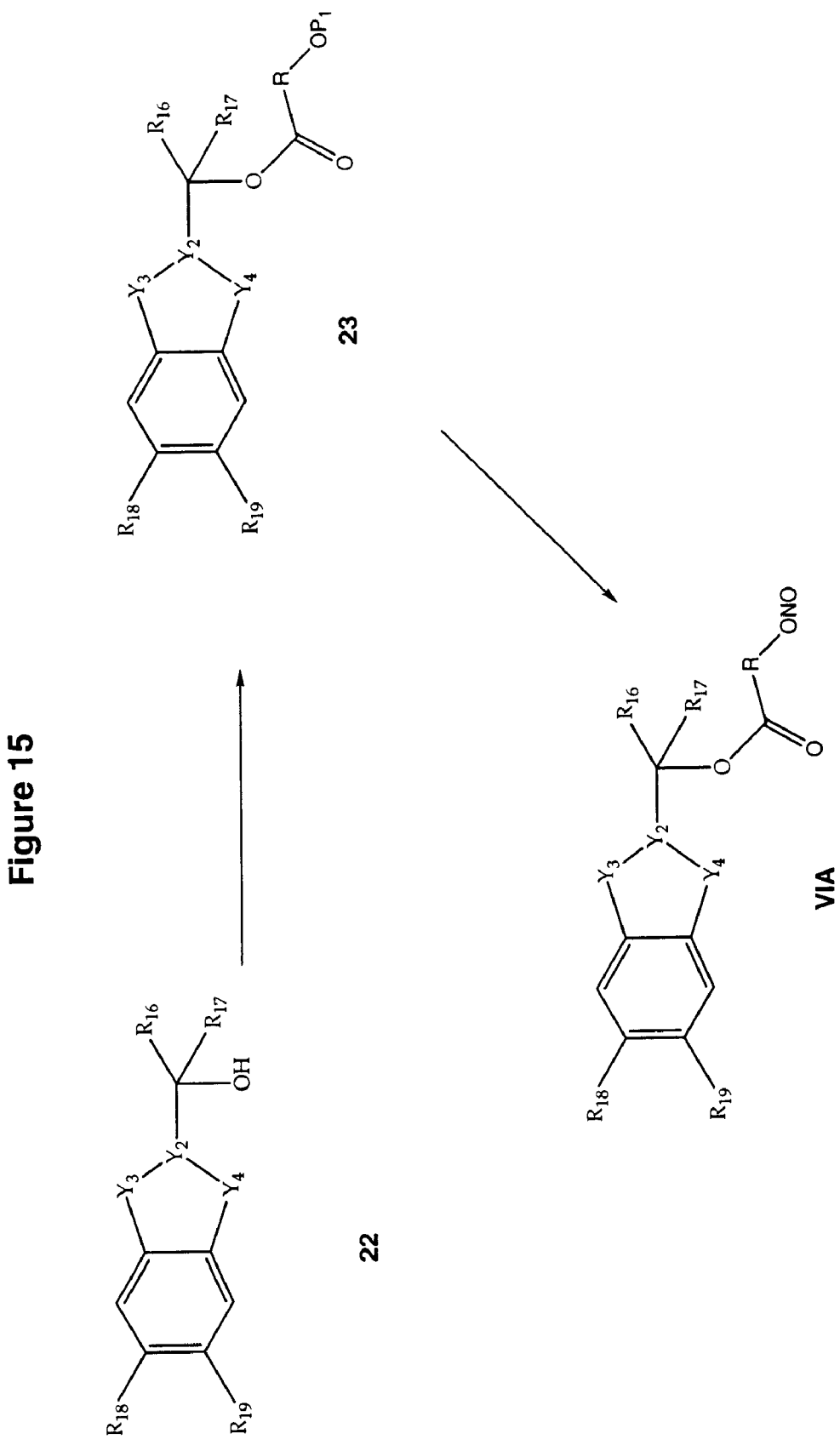
FIG. 15 is the synthetic scheme for the preparation of a nitrite containing acyl group of Formula (VI).

Nitroso compounds of Formula (VI) wherein $Y_2$, $Y_3$, $Y_4$, $R_{14}$, $R_{15}$, $R_{16}$ and $R_{17}$ are defined as herein and a nitrite containing acyl group is representative of the $D_2$ group as defined herein can be prepared as outlined in FIG. 15. The alcohol of structure 22 is converted to the acyl derivative of the structure 23 wherein R is as defined herein by reaction with an appropriate protected alcohol containing activated acylating agent wherein $P^1$ is as defined herein. Preferred methods for the formation of esters is reacting the alcohol with the preformed acid chloride or symmetrical anhydride of the protected alcohol containing acid or condensing the alcohol and protected alcohol containing acid in the presence of a dehydrating agent such as dicyclohexylcarbodiimide (DCC) or 1-ethyl-3 (3-dimethyl-aminopropyl) carbodiimide hydrochloride (EDAC HCl) with a catalyst such as 4-dimethylaminopyridine (DMAP) or 1-hydroxybenzotriazole (HOBt). Preferred protecting groups for the alcohol moiety are silyl ethers such as a trimethylsilyl or tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloro-methane, THF, DMF, or acetonitrile with or without an amine base such as pyridine or triethylamine affords the compound of the structure VIA.

Figure 16:
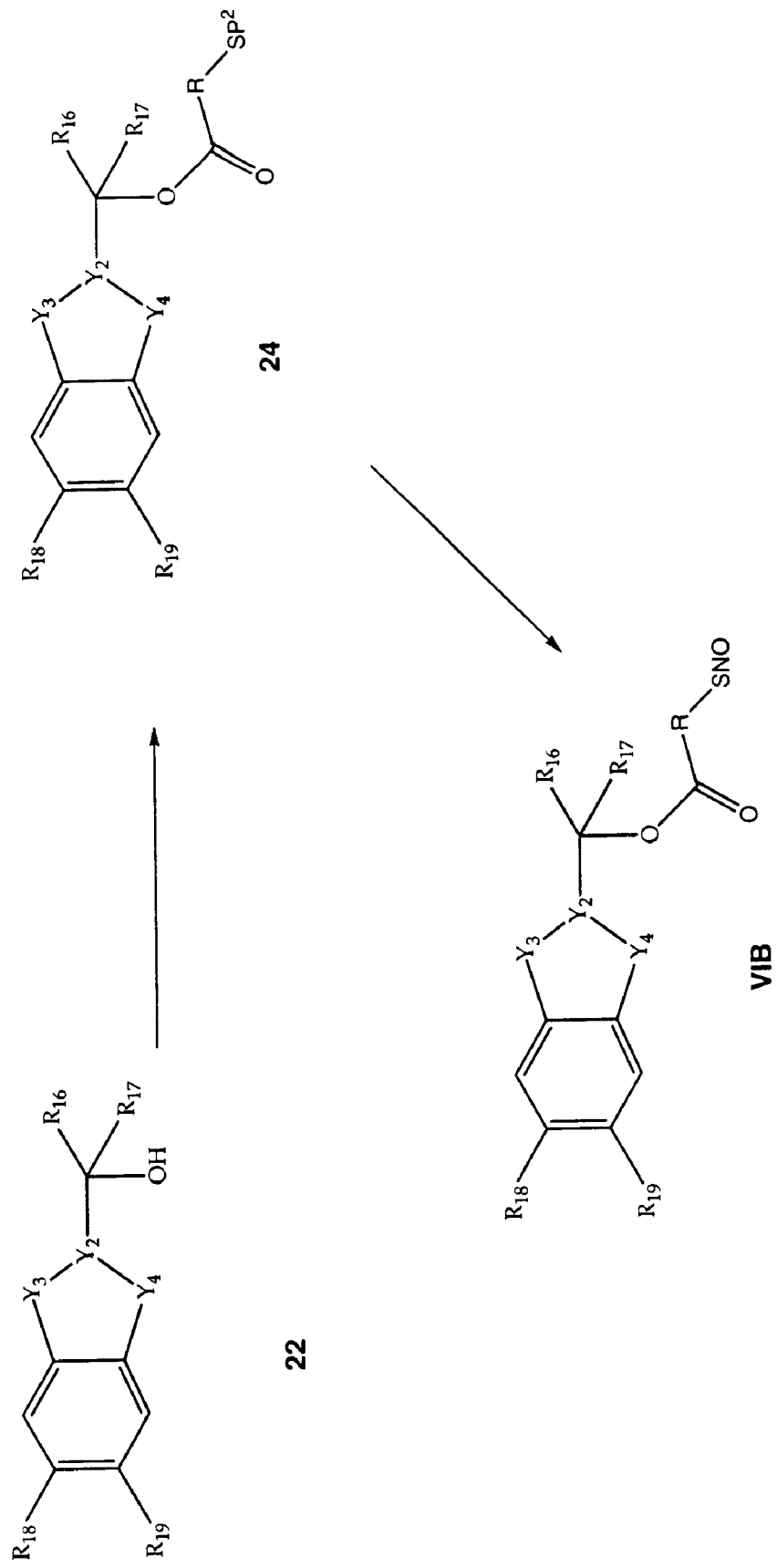
FIG. 16 is the synthetic scheme for the preparation of a nitrosothiol containing acyl group of Formula (VI).

Nitroso compounds of Formula (VI) wherein $Y_2$, $Y_3$, $Y_4$, $R_{14}$, $R_{15}$, $R_{16}$ and $R_{17}$ are defined as herein and a nitrosothiol containing acyl group is representative of the $D_2$ group as defined herein can be prepared as outlined in FIG. 16. The alcohol of structure 22 is converted to the acyl derivative of the structure 24 wherein R is as defined herein by reaction with an appropriate protected thiol containing activated acylating agent wherein $P^2$ is as defined herein. Preferred methods for the formation of esters are reacting the alcohol with the preformed acid chloride or symmetrical anhydride of the protected thiol containing acid or condensing the alcohol and protected thiol containing acid in the presence of a dehydrating agent such as dicyclohexylcarbodiimide (DCC) or 1-ethyl-3 (3-dimethyl-aminopropyl) carbodiimide hydrochloride (EDAC HCl) with a catalyst such as 4-dimethylaminopyridine (DMAP) or 1-hydroxybenzotriazole (HOBt). Preferred protecting groups for the thiol moiety are as a thioester, such as thioacetate or thiobenzoate, as a disulfide, as a thiocarbamate, such as N-methoxymethyl thiocarbamate, or as a thioether, such as paramethoxybenzyl thioether, a 2,4, 6-trimethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate or strong acids such as trifluoroacetic or hydrochloric acid and heat are used to remove a paramethoxybenzyl thioether, a 2,4,6-trimethoxybenzyl thioether a tetrahydropyranyl thioether or a S-triphenylmethyl thioether group) followed by reaction with a suitable nitrosylating agent, such as thionyl chloride nitrite, thionyl dinitrite, a lower alkyl nitrite, such as tert-butyl nitrite, or nitrosium tetrafluoroborate, in a suitable anhydrous solvent, such as methylene chloride, THF, DMF or acetonitrile, with or without an amine base, such as pyridine or triethylamine, produces the compounds of structure VIB. Alternatively, a stoichiometric quantity of sodium nitrite in alcoholic or aqueous acid produces the compounds of structure VIB.

The compounds of the present invention include potassium channel activators, including those described herein, which have been nitrosated and/or nitrosylated through one or more sites such as oxygen (hydroxyl condensation), sulfur (sulfhydryl condensation), carbon and/or nitrogen. The nitrosated and/or nitrosylated potassium channel activators of the present invention donate, transfer or release a biologically active form of nitrogen monoxide (nitric oxide).

Nitrogen monoxide can exist in three forms: NO— (nitroxyl), NO. (nitric oxide) and $NO^+$ (nitrosonium). NO. is a highly reactive short-lived species that is potentially toxic to cells. This is critical because the pharmacological efficacy of NO depends upon the form in which it is delivered. In contrast to the nitric oxide radical (NO.), nitrosonium ($NO^+$) does not react with $O_2$ or $O_2$— species, and functionalities capable of transferring and/or releasing $NO^+$ and NO— are also resistant to decomposition in the presence of many redox metals. Consequently, administration of charged NO equivalents (positive and/or negative) does not result in the generation of toxic by-products or the elimination of the active NO moiety.

Compounds contemplated for use in the present invention (e.g., potassium channel activators and/or nitrosated and/or nitrosylated potassium channel activators) are, optionally, used in combination with nitric oxide and compounds that release nitric oxide or otherwise directly or indirectly deliver or transfer nitric oxide to a site of its activity, such as on a cell membrane in vivo.

The term "nitric oxide" encompasses uncharged nitric oxide (NO.) and charged nitrogen monoxide species, preferably charged nitrogen monoxide species, such as nitrosonium ion ($NO^+$) and nitroxyl ion (NO—). The reactive form of nitric oxide can be provided by gaseous nitric oxide. The nitric oxide releasing, delivering or transferring compounds, have the structure F—NO, wherein F is a nitric oxide releasing, delivering or transferring moiety, include any and all such compounds which provide nitric oxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines (NONOates), (E)-alkyl-2-[(E)-hydroxyimino]-5-nitro-3-hexene amines or amides, nitrosoamines, furoxans as well as substrates for the endogenous enzymes which synthesize nitric oxide. The "NO adducts" can be mono-nitrosylated, poly-nitrosylated, mono-nitrosated and/or poly-nitrosated or a combination thereof at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3):165–198 (1983), the disclosures of each of which are incorporated by reference herein in their entirety.

Another embodiment of the present invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine and S-nitroso-glutathione.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS(C(R_e)(R_f))_m SNO$;

(ii) $ONS(C(R_e)(R_f))_m R_e$; and (iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, -T-Q, or $(C(R_e)(R_f))_k$-T-Q, or $R_e$ and $R_f$ taken together with the carbons to which they are attached form a carbonyl, a methanthial, a heterocyclic ring, a cycloalkyl group or a bridged cycloalkyl group; Q is —NO or —NO$_2$; and T is independently a covalent bond, a carbonyl, an oxygen, —S(O)$_o$— or —N(R$_a$)R$_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$—C(T-Q)(R$_e$)(R$_f$), or —(N$_2$O$_2$—)$^-$.M$^+$, wherein M$^+$ is an organic or inorganic cation; with the proviso that when $R_i$ is —CH$_2$—C(T-Q)(R$_e$)(R$_f$) or —(N$_2$O$_2$—).M$^+$; then "-T-Q" can be a hydrogen, an alkyl group, an alkoxyalkyl group, an aminoalkyl group, a hydroxy group or an aryl group.

In cases where $R_e$ and $R_f$ are a heterocyclic ring or $R_e$ and $R_f$ when taken together with the carbon atoms to which they are attached are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with NaNO$_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetraflurorborate in an inert solvent.

Another group of NO adducts for use in the present invention, where the NO adduct is a compound that donates, transfers or releases nitric oxide, include compounds comprising at least one ON—O—, ON—N— or ON—C— group. The compounds that include at least one ON—O—, ON—N— or ON—C— group are preferably ON—O—, ON—N— or ON—C-polypeptides (the term "polypeptide" includes proteins and polyamino acids that do not possess an ascertained biological function, and derivatives thereof; ON—O, ON—N— or ON—C-amino acids (including natural and synthetic amino acids and their stereoisomers and racemic mixtures); ON—O—, ON—N— or ON—C-sugars; ON—O—, ON—N— or ON—C— modified or unmodified oligonucleotides (comprising at least 5 nucleotides, preferably 5–200 nucleotides); ON—O—, ON—N— or ON—C— straight or branched, saturated or unsaturated, aliphatic or aromatic, substituted or unsubstituted hydrocarbons; and ON—O—, ON—N— or ON—C— heterocyclic compounds.

Another group of NO adducts for use in the present invention include nitrates that donate, transfer or release nitric oxide, such as compounds comprising at least one O$_2$N—O—, O$_2$N—N—, O$_2$N—S— or O$_2$N—C— group. Preferred among these compounds are O$_2$N—O—, O$_2$N—N—, O$_2$N—S— or O$_2$N—C— polypeptides (the term "polypeptide" includes proteins and also polyamino acids that do not possess an ascertained biological function, and derivatives thereof; O$_2$N—O—, O$_2$N—N—, O$_2$N—S— or O$_2$N—C— amino acids (including natural and synthetic amino acids and their stereoisomers and racemic mixtures); O$_2$N—O—, O$_2$N—N—, O$_2$N—S— or O$_2$N—C-sugars; O$_2$N—O—, O$_2$N—N—, O$_2$N—S— or O$_2$N—C— modified and unmodified oligonucleotides (comprising at least 5 nucleotides, preferably 5–200 nucleotides); O$_2$N—O—, O$_2$N—N—, O$_2$N—S— or O$_2$N—C— straight or branched, saturated or unsaturated, aliphatic or aromatic, substituted or unsubstituted hydrocarbons; and O$_2$N—O—, O$_2$N—N—, O$_2$N—S— or O$_2$N—C— heterocyclic compounds. Preferred examples of compounds comprising at least one O$_2$N—O—, O$_2$N—N—, O$_2$N—S— or O$_2$N—C— group include isosorbide dinitrate, isosorbide mononitrate, clonitrate, erythrityltetranitrate, mannitol hexanitrate, nitroglycerin, pentaerythritoltetranitrate, pentrinitrol and propatylnitrate.

Another group of NO adducts are N-oxo-N-nitrosoamines that donate, transfer or release nitric oxide and are represented by the formula: $R^1R^2$—N(O—M$^+$)—NO, where $R^1$ and $R^2$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and $M^+$ is as defined herein.

Another group of NO adducts are thionitrates that donate, transfer or release nitric oxide and are represented by the formula: $R^1$—(S)—$NO_2$, where $R^1$ is a polypeptide, an amino acid, a sugar, a modified or unmodified oligonucleotide, a straight or branched, saturated or unsaturated, aliphatic or aromatic, substituted or unsubstituted hydrocarbon, or a heterocyclic group. Preferred are those compounds where $R^1$ is a polypeptide or hydrocarbon with a pair or pairs of thiols that are sufficiently structurally proximate, i.e., vicinal, that the pair of thiols will be reduced to a disulfide. Compounds which form disulfide species release nitroxyl ion (NO—) and uncharged nitric oxide (NO.).

The present invention is also directed to compounds that stimulate endogenous NO or elevate levels of endogenous endothelium-derived relaxing factor (EDRF) in vivo or are substrates for the enzyme, nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid) and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature,* 327:524–526 (1987); Ignarro et al, *Proc. Natl. Acad. Sci. USA,* 84:9265–9269 (1987)).

The present invention is also based on the discovery that the administration of a therapeutically effective amount of the compounds and compositions described herein is effective for treating or preventing sexual dysfunctions or enhancing sexual responses in patients, including males and females. For example, the patient can be administered a therapeutically effective amount of at least one nitrosated and/or nitrosylated potassium channel activator of the present invention. In another embodiment, the patient can be administered a therapeutically effective amount of at least one potassium channel activator, optionally substituted with at least one NO and/or $NO_2$ group, and at least one compound that donates, transfers or releases nitric oxide as a charged species, or elevates levels of endogenous EDRF or nitric oxide, or is a substrate for nitric oxide synthase. In yet another embodiment, the patient can be administered a therapeutically effective amount of at least one potassium channel activator, optionally substituted with at least one NO and/or $NO_2$ group, and at least one vasoactive agent, and, optionally, at least one compound that donates, transfers or releases nitric oxide as a charged species, or elevates levels of endogenous EDRF or nitric oxide, or is a substrate for nitric oxide synthase. The compounds can be administered separately or in the form of a composition.

A vasoactive agent is any therapeutic agent capable of relaxing vascular smooth muscle. Suitable vasoactive agents include, but are not limited to, calcium blockers (such as, for example, nifedipine, veraparmil, diltiazem, gallopamil, niludipine, nimodipins, nicardipine, and the like); β-blockers (such as, for example, butixamine, dichloroisoproterenol, propanolol, alprenolol, bunolol, nadolol, oxprenolol, perbutolol, pinodolol, sotalol, timolol, metoprolol, atenolol, acebutolol, bevantolol, pafenolol, tolamodol, and the like); long and short acting α-adrenergic receptor antagonist (such as, for example, phenoxybenzamide, dibenamine, doxazosin, terazosin, phentolamine, tolazoline, prozosin, trimazosin, yohimbine, moxisylyte and the like); phosphodiesterase inhibitors (such as, for example, papaverine, zaprinast, sildenafil, IC 351 and the like); adenosine, ergot alkaloids (such as, for example, ergotamine, ergotamine analogs, including, for example, acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride and the like); vasoactive intestinal peptides (such as, for example, peptide histidine isoleucine, peptide histidine methionine, substance P, calcitonin gene-related peptide, neurokinin A, bradykinin, neurokinin B, and the like); dopamine agonists (such as, for example, apomorphine, bromocriptine, testosterone, cocaine, strychnine, and the like); opioid antagonists (such as, for example, naltrexone, and the like); prostaglandins (such as, for example, alprostadil, prostaglandin $E_2$, prostaglandin $F_2$, misoprostol, enprostil, arbaprostil, unoprostone, trimoprostil, carboprost, limaprost, gemeprost, lantanoprost, ornoprostil, beraprost, sulpostrone, rioprostil, and the like); endothelin antagonists (such as, for example, bosentan, sulfonamide endothelin antagonists, BQ-123, SQ 28608, and the like); thromboxane inhibitors (such as, for example, SQ 29548, BAY u3405, GR 32191, YM 158, and the like), and mixtures thereof.

Another embodiment of the present invention provides methods to prevent or treat cardiovascular disorders, such as congestive heart failure and myocardial ischemia, especially angina pectoris and arrhythmia; cerebrovascular disorders including those associated with cerebral ischemia; hypertension; asthma; baldness; urinary incontinence; epilepsy; sleep disorders; gastrointestinal disorders; migraines; irritable bowel syndrome and sensitive skin, by administering to a patient in need thereof a therapeutically effective amount of the compounds and/or compositions described herein. For example, the patient can be administered a therapeutically effective amount of at least one nitrosated and/or nitrosylated potassium channel activator of the present invention. In another embodiment, the patient can be administered a therapeutically effective amount of at least one potassium channel activator, optionally substituted with at least one NO and/or $NO_2$ group, and at least one compound that donates, transfers or releases nitric oxide as a charged species, or elevates levels of endogenous EDRF or nitric oxide or is a substrate for nitric oxide synthase. In yet another embodiment, the patient can be administered a therapeutically effective amount of at least one potassium channel activator, optionally substituted with at least one NO and/or $NO_2$ group, and at least one vasoactive agent, and, optionally, at least one compound that donates, transfers or releases nitric oxide as a charged species, or elevates levels of endogenous EDRF or nitric oxide or is a substrate for nitric oxide synthase. The potassium channel activators optionally substituted with at least one NO and/or $NO_2$ group, nitric oxide donors and/or vasoactive agents can be administered separately or in the form of a composition. The compounds and compositions of the present invention can also be administered in combination with other medications used for the treatment of these disorders.

When administered in vivo, the compounds and compositions of the present invention can be administered in combination with pharmaceutically acceptable carriers and in dosages described herein. When the compounds and compositions of the present invention are administered as a mixture of at least one nitrosated and/or nitrosylated potassium channel activator or at least one potassium channel activator and at least one nitric oxide donor, they can also be used in combination with one or more additional compounds which are known to be effective against the specific disease state targeted for treatment (e.g., vasoactive agents). The nitric oxide donors and/or vasoactive agents can be administered simultaneously with, subsequently to, or prior to administration of the potassium channel activators, including those that are substituted with one or more NO and/or $NO_2$ groups, and/or other additional compounds.

The compounds and compositions of the present invention can be administered by any available and effective delivery system including, but not limited to, orally, bucally, parenterally, by inhalation spray (oral or nasal), by topical application, by injection into the corpus cavernosum tissue, by transurethral drug delivery, vaginally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous injections, intramuscular injections, intrasternal injections, and infusion techniques. Parenteral also includes injection into the corpus cavernosum tissue, which can be conducted using any effective injection system including, but not limited to, conventional syringe-and-needle systems or needleless injection devices.

Topical administration, which is well known to one skilled in the art, involves the delivery of pharmaceutical agents via percutaneous passage of the drug into the systemic circulation of the patient. Topical administration includes vaginal administration, vulval administration, penile administration and rectal administration. Topical administration can also involve transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like.

Dosage forms for topical administration of the compounds and compositions of the present invention preferably include creams, sprays, lotions, gels, ointments, emulsions, coatings for condoms, liposomes, foams, and the like. Administration of the cream, spray, lotion, gel, ointment, emulsion, coating, liposome, or foam can be accompanied by the use of an applicator or by transurethral drug delivery using a syringe with or without a needle or penile insert or device, or by clitoral, vulval or vaginal delivery, and is within the skill of the art. Typically a lubricant and/or a local anesthetic for desensitization can also be included in the formulation or provided for use as needed. Lubricants include, for example, K-Y jelly (available from Johnson & Johnson) or a lidocaine jelly, such as XYLOCAINE® 2% jelly (available from Astra Pharmaceutical Products). Local anesthetics include, for example, novocaine, procaine, tetracaine, benzocaine and the like.

Solid dosage forms for oral administration can include capsules, tablets, effervescent tablets, chewable tablets, pills, powders, effervescent powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the present invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention can be prepared by mixing the compounds or compositions with a suitable nonirritating excipient such as cocoa butter and polyethylene glycols which are solid at room temperature but liquid at body temperature, such that they will melt and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compounds and compositions of the present invention will typically be administered in a pharmaceutical composition containing one or more carriers or excipients, i.e., pharmaceutically acceptable organic or inorganic carrier substances suitable for parenteral application which do not deleteriously react with the active compounds. Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyinylpyrrolidone, and the like. The compositions can also include one or more permeation enhancers including, for example, dimethylsulfoxide (DMSO), dimethyl formamide (DMF), N,N-dimethylacetamide (DMA), decylmethylsulfoxide (C10MSO), polyethylene glycol monolaurate (PEGML), glyceral monolaurate, lecithin, 1-substituted azacycloheptan-2-ones, particularly 1-N-dodecylcyclazacylcoheptan-2-ones (available under the trademark Azone™ from Nelson Research & Development Co., Irvine, Calif.), alcohols and the like.

The pharmaceutical preparations can be sterilized and if desired, mixed with auxiliary agents which do not deleteriously react with the active compounds, e.g., lubricants, preservatives, stabilizers, wetting agents, emulsifiers, salts for influencing osmotic pressure, buffers, colorings, flavoring and/or aromatic substances, and the like. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the present invention, including, for example, encapsulation in liposomes, microbubbles, emulsions, microparticles, microcapsules and the like. The required dosage can be administered as a single unit or in a sustained release form.

The bioavailabilty of the compositions can be enhanced by micronization of the formulations using conventional techniques such as grinding, milling, spray drying and the like in the presence of suitable excipients or agents such as phospholipids or surfactants. The bioavailability and absorption of the potassium channel activators can be increased by the addition of tabletting excipients, such as, for example β-cyclodextrin, a β-cyclodextrin derivative, such as for example, hydroxypropyl-β-cyclodextrin (HPBCD), and the like.

The compounds and compositions of the present invention can be formulated as pharmaceutically acceptable salts. Pharmaceutically acceptable salts include, for example, alkali metal salts and addition salts of free acids or free bases. The nature of the salt is not critical, provided that it is pharmaceutically acceptable. Suitable pharmaceutically acceptable acid addition salts may be prepared from an inorganic acid or from an organic acid. Examples of such inorganic acids include, but are not limited to, hydrochloric, hydrobromic, hydroiodic, nitric (nitrate salt), nitrous (nitrite salt), carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, β-hydroxybenzoic, phenylacetic, mandelic, embonic (pamoic), methanesulfonic, ethanesulfonic, benzenesulfonic, pantothenic, toluenesulfonic, 2-hydroxyethanesuifonic, sulfanilic, stearic, algenic, β-hydroxybutyric, cyclohexylaminosulfonic, galactaric and galacturonic acid and the like. Suitable pharmaceutically acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

"Therapeutically effective amount" refers to the amount of the potassium channel activator, nitrosated and/or nitrosylated potassium channel activator, nitric oxide donor and/or vasoactive agent that is effective to achieve its intended purpose. While individual patient needs may vary, determination of optimal ranges for effective amounts of each of the compounds and compositions is within the skill of the art. Generally the dosage regimen for treating a condition with the compounds and/or compositions of this invention is selected in accordance with a variety of factors, including the type, age, weight, sex, diet and medical condition of the patient, the severity of the dysfunction, the route of administration, pharmacological considerations such as the activity, efficacy, pharmacokinetic and toxicology profiles of the particular compound used, whether a drug delivery system is used, and whether the compound is administered as part of a drug combination and can be adjusted by one skilled in the art. Thus, the dosage regimen actually employed may vary from the preferred dosage regimen set forth herein.

The amount of a given potassium channel activator (including nitrosated and/or nitrosylated potassium channel activators) which will be effective in the prevention or treatment of a particular dysfunction or condition will depend on the nature of the dysfunction or condition, and can be determined by standard clinical techniques, including reference to Goodman and Gilman, supra; The Physician's Desk Reference, supra; Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the dysfunction or disorder, and should be decided by the physician and the patient's circumstances. Effective doses may be extrapolated from dose-response curves derived from in vitro or animal model test systems and are in the same ranges or less than as described for the commercially available compounds in the Physician's Desk Reference, supra.

The usual doses of potassium channel activators (including nitrosated and/or nitrosylated potassium channel activators) for intracavernosal injection are about 0.001 mg/kg to about 30 mg/kg, and preferably about 0.01 mg/kg to about 25 mg/kg. The oral dose of potassium channel activators (including nitrosated and/or nitrosylated potassium channel activators) are about 1 mg to about 100 mg preferably about 5 mg to about 80 mg.

The doses of nitric oxide donors in the pharmaceutical composition can be in amounts of about 0.001 mg to about 30 g and the actual amount administered will be dependent on the specific nitric oxide donor compound. For example, when L-arginine is the nitric oxide donor, L-arginine can be administered orally in an amount of about 0.25 grams to about 10 grams (equivalent to about 0.5 grams to about 20 grams of L-arginine glutamate), preferably about 2 grams to about 4 grams (equivalent to about 4 grams to about 8 grams of L-arginine glutamate); more preferably about 2.5 grams to about 3.5 grams (equivalent to about 5 grams to about 7 grams of L-arginine glutamate); most preferably about 3 grams (equivalent to 6 grams of L-arginine glutamate).

The nitrosated and/or nitrosylated potassium channel activators of the invention are used at dose ranges and over a course of dose regimen and are administered in the same or substantially equivalent vehicles/carrier by the same or substantially equivalent as their non-nitrosated/nitrosylated counterparts. The nitrosated and/or nitrosylated compounds of the invention can also be used in lower doses and in less extensive regimens of treatment. The amount of active ingredient that can be combined with the carrier materials to produce a single dosage form will vary depending upon the host treated and the particular mode of administration.

Particularly preferred methods of administration of the contemplated potassium channel activator compositions (including nitrosated and/or nitrosylated potassium channel activator compositions) for the treatment of male sexual dysfunction are topical application, by injection into the corpus cavernosum, by transurethral administration or by the use of suppositories. The preferred methods of administration for female sexual dysfunction are topical application or by the use of suppositories.

The present invention also provides pharmaceutical kits comprising one or more containers filled with one or more of the ingredients of the pharmaceutical compounds and/or compositions of the present invention, including, one or more potassium channel activators, optionally substituted with one or more NO and/or $NO_2$ groups, and one or more of the NO donors, and one or more vasoactive agents described herein. Such kits can also include, for example, other compounds and/or compositions (e.g., vasoactive agents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

EXAMPLE

The following non-limiting example is for purposes of illustration only and is not intended to limit the scope of the invention or claims.

Example 1

N-[2-methyl-2-(nitrosothio)propyl]-3-pyridylcarboxamide

1a N-(2-methyl-2-sulfanylpropyl)-3-pyridylcarboxamide

1-Amino-2-methylpropane-2-thiol hydrochloride (1.10 g, 6.18 mmol) was dissolved in DMF and nicotinoyl chloride hydrochloride (1.14 g, 8.03 mmol) was slowly added as a solid. The mixture was cooled to 0° C. and triethylamine (3.0 mL, 21.63 mmol) was slowly added. The mixture was stirred for one half hour at 0° C., allowed to warm to room temperature, and stirred overnight. The reaction mixture was diluted with methylene chloride, washed with saturated sodium bicarbonate, brine, and dried over magnesium sulfate. The volatiles were removed under reduced pressure to give a pink oil. An excess of hydrogen chloride in ether was added to precipitate 831 mg. (55%) of the title compound, mp. 163–165° C. $^1$H NMR (300 MHz, DMSO) δ 9.00 (br s, 1H), 8.71 (dd, 1H, J=2.0,4.9), 8.20 (dt, 1H, j=2.0, 7.9), 7.51 (dd, 1H, J=4.9, 7.9), 3.44 (d, 2H, J=6.3), 1.32 (s, 6H).

1b. N-[2-methyl-2-(nitrosothio)propyl]-3-pyridylcarboxamide

The compound of Example 1a (73.5 mg, 0.298 mmol) was dissolved in methanol and tert-butylnitrite (38.3 mg, 0.328 mmol) was added. The mixture was stirred for 45 minutes and the solvent removed under reduced pressure. An excess of hydrogen chloride in ether was added to precipitate 45.2 mg (90%) of the title compound, mp. 125–127° C. $^1$H NMR (300 MHz, DMSO) δ 9.03 (br s, 1H), 8.73 (dd, 1, 2H, J=1.5,4.8), 8.22 (br d, 1H, J=7.9), 7.53 (dd, 1H, J=4.8,7.9) 3.47 (d, 2H, J=6.3), 1.34 (s, 6H).

The disclosure of each patent, patent application and publication cited in the specification is hereby incorporated by reference herein in its entirety.

Although the invention has been set forth in detail, one skilled in the art will appreciate that numerous changes and modifications can be made to the invention without departing from the spirit and scope thereof.

What is claimed is:

1. A compound of Formula (II), or a pharmaceutically acceptable salt thereof:

wherein the compound of Formula (II) is:

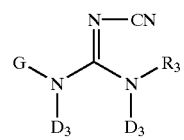

(II)

wherein $R_3$ is a hydrogen, an alkyl, an aryl, an alkylaryl or K;

$D_3$ is a hydrogen or $D_2$, with the proviso that at least one $D_3$ must be designated as $D_2$ if $R_3$ is not K;

G is:

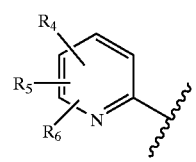

(1)

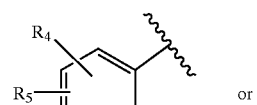

(2)

or

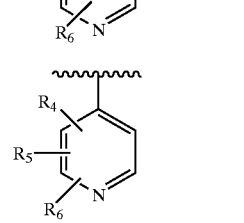

(3)

$R_4$, $R_5$, and $R_6$ are each independently a hydrogen, a halogen, a hydroxy, a lower alkyl, an alkoxy, a nitrile, a nitrite, a carboxyamido, a carboxylic ester, an alkylsulfinyl, an arylsulfinyl, an aminoalkyl, an alkylthio, or an arylthio; or $R_5$ and R taken together are a group which forms a ring with the two carbon atoms to which they are attached, wherein the group is —S(O)$_t$—(CH$_2$)$_r$—CH$_2$—, —C(O)Z-(CH$_2$)$_o$—CH$_2$, or —C(O)—CH$_2$—(CH$_2$)$_o$—Z-;

t is an integer of 1 or 2;

r is an integer from 1 to 3;

Z is oxygen, NR$_7$ or CH$_2$;

R$_7$ is hydrogen or R$_3$;

D$_2$ is Q or K;

Q is —NO or —NO$_2$;

K is —W$_a$-E$_b$-(C(R$_e$)(R$_f$))$_p$-E$_c$-(C(R$_e$)(R$_f$))$_x$—W$_d$—(C(R$_e$)(R$_f$))$_y$—W$_i$-E$_j$-W$_g$(C(R$_e$)(R$_f$))$_z$-T-Q;

a, b, c, d, g, i and j are each independently an integer from 0 to 3;

p, x, y and z are each independently an integer from 0 to 10;

W at each occurrence is independently —C(O)—, —C(S)—, -T-, —(C(R$_e$)(R$_f$))$_h$—, an alkyl group, an aryl group, a heterocyclic ring, an arylheterocyclic ring, or —(CH$_2$CH$_2$O)$_q$—;

E at each occurrence is independently -T-, an alkyl group, an aryl group, —(C(R$_e$)(R$_f$))$_h$—, a heterocyclic ring, an arylheterocyclic ring, or —(CH$_2$CH$_2$O)$_q$—;

h is an integer from 1 to 10;

q is an integer from 1 to 5;

R$_e$ and R$_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, -T-Q, or (C(R$_e$)(R$_f$))$_k$-T-Q, or R$_e$ and R$_f$ taken together with the carbon atom to which they are attached form a carbonyl, a methanthial, a cycloalkyl group or a bridged cycloalkyl group;

k is an integer from 1 to 3;

T at each occurrence is independently a covalent bond, a carbonyl, an oxygen, —S(O)$_o$— or —N(R$_a$)R$_i$—;

o is an integer from 0 to 2;

R$_a$ is a lone pair of electrons, a hydrogen or an alkyl group;

R$_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$—C(T-Q)(R$_e$)(R$_f$), or —(N$_2$O$_2$—)$^-$.M$^+$, wherein M$^+$ is an organic or inorganic cation; with the proviso that when R$_i$ is —CH$_2$—C(T-Q)(R$_e$)(R$_f$) or —(N$_2$O$_2$)$^-$.M$^+$, or R$_e$ or R$_f$ are T-Q or (C(R$_e$)(R$_f$))$_k$-T-Q, then the "-T-Q" subgroup can be a hydrogen, an alkyl, an alkoxy, an alkoxyalkyl, an aminoalkyl, a hydroxy, a heterocyclic ring or an aryl group; with the proviso that when the T in "-T-Q" is oxygen then Q is not —NO$_2$; and with the proviso that the compound of Formula (II) must contain at least one NO group, at least one NO$_2$ group or at least one NO group and NO$_2$ group; wherein the at least one NO group, the at least one NO$_2$ group or the at least one NO group and NO$_2$ group is linked to the compound of Formula (II) through an oxygen, sulfur or nitrogen atom.

2. The compound of claim 1, wherein the compound of Formula (II) is a nitrosated pinacidil, a nitrosylated pinacidil or a nitrosated and nitrosylated pinacidil.

3. A composition comprising the compound of claim 1 and a pharmaceutically acceptable carrier.

4. A method for treating a sexual dysfunction in a patient in need thereof comprising administering to the patient a therapeutically effective amount of the composition of claim 3.

5. The method of claim 4, wherein the patient is female.

6. The method of claim 4, wherein the patient is male.

7. The method of claim 4, wherein the composition is administered by intracavernosal injection, by transurethral application or topically.

8. The method of claim 7, wherein the composition is administered topically in the form of a cream, a spray, a lotion, a gel, an ointment, an emulsion, a foam, a coating for a condom, or a liposome composition.

9. A method for treating a cardiovascular disorder, a cerebrovascular disorder, hypertension, asthma, baldness, urinary incontinence, epilepsy, a gastrointestinal disorder, or an irritable bowel syndrome in a patient in need thereof comprising administering to the patient a therapeutically effective amount of the composition of claim 3.

10. The composition of claim 3, further comprising at least one vasoactive agent.

11. A The composition of claim 10, wherein the vasoactive agent is a calcium channel blocker, an α-adrenergic receptor antagonist, a β-blocker, a phosphodiesterase inhibitor, adenosine, an ergot alkaloid, a vasoactive intestinal peptide, a prostaglandin, a dopamine agonist, an opioid antagonist, an endothelin antagonist, a thromboxane inhibitor or a mixture thereof.

12. A method for treating a sexual dysfunction in a patient in need thereof comprising administering to the patient a therapeutically effective amount of the composition of claim 10.

13. The method of claim 12, wherein the patient is female.

14. The method of claim 12, wherein the patient is male.

15. The method of claim 12, wherein the composition is administered by intracavernosal injection, by transurethral application or topically.

16. The method of claim 15, wherein the composition is administered topically in the form of a cream, a spray, a lotion, a gel, an ointment, an emulsion, a foam, a coating for a condom, or a liposome composition.

17. A method for treating a cardiovascular disorder, a cerebrovascular disorder, hypertension, asthma, baldness, urinary incontinence, epilepsy, a gastrointestinal disorder, or an irritable bowel syndrome in a patient in need thereof comprising administering to the patient a therapeutically effective amount of the composition of claim 10.

18. A composition comprising at least one compound of claim 1 and at least one compound that donates, transfers, or releases nitric oxide, induces the production of endogenous nitric oxide or endothelium-derived relaxing factor, stimulates endogenous synthesis of nitrogen monoxide or is a substrate for nitric oxide synthase or a pharmaceutically acceptable salt thereof.

19. The composition of claim 18, wherein the at least one compound that donates, transfers, or releases nitric oxide, induces the production of endogenous nitric oxide or endothelium-derived relaxing factor, stimulates endogenous synthesis of nitrogen monoxide or is a substrate for nitric oxide synthase is an S-nitrosothiol.

20. The composition of claim 19, wherein the S-nitrosothiol is S-nitroso-N-acetylcysteine, S-nitroso-captopril, S-nitroso-N-acetylpenicillamine; S-nitroso-homocysteine, S-nitroso-cysteine or S-nitroso-glutathione.

21. The composition of claim 19, wherein the S-nitrosothiol is:

(i) HS(C(R$_e$)(R$_f$))$_m$SNO;

(ii) ONS(C(R$_e$)(R$_f$))$_m$R$_e$; and (iii) H$_2$N—CH(CO$_2$H)—(CH$_2$)$_m$—C(O)NH—CH(CH$_2$SNO)—C(O)NH—CH$_2$—CO$_2$H;

wherein m is an integer from 2 to 20; R$_e$ and R$_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, an alkylcarboxamido, an arylcarboxamido, an amidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, -T-Q, or $(C(R_e)(R_f))_k$-T-Q, or $R_e$ and $R_f$ taken together with the carbon atom to which they are attached form a carbonyl, a methanthial, a cycloalkyl group or a bridged cycloalkyl group; Q is —NO or —NO$_2$; and T is independently a covalent bond, a carbonyl, an oxygen, —S(O)$_o$— or —N($R_a$)$R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$—C(T-Q)(R$_e$)(R$_f$), or —(N$_2$O$_2$—).M$^+$, wherein M$^+$ is an organic or inorganic cation; with the proviso that when $R_i$ is —CH$_2$—C(T-Q)(R$_e$)(R$_f$) or —(N$_2$O$_2$—).M$^+$; then "-T-Q" can be a hydrogen, an alkyl group, an alkoxyalkyl group, an aminoalkyl group, a hydroxy group or an aryl group.

22. The composition of claim 18, wherein the at least one compound that donates, transfers, or releases nitric oxide, induces the production of endogenous nitric oxide or endothelium-derived relaxing factor, stimulates endogenous synthesis of nitrogen monoxide or is a substrate for nitric oxide synthase is:
(i) a compound that comprises at least one ON—O—, ON—N— or ON—C— group;
(ii) a compound that comprises at least one O$_2$N—O—, O$_2$N—N—, O$_2$N—S— or —O$_2$N—C— group;
(iii) a N-oxo-N-nitrosoamine having the formula: R$^1$R$^2$N—N(O—M$^+$)—NO, wherein R$^1$ and R$^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and M$^+$ is an organic or inorganic cation.

23. The composition of claim 22, wherein the compound comprising at least one ON—O—, ON—N— or ON—C— group is an ON—O-polypeptide, an ON—N-polypepetide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, an ON—O-heterocyclic compound, an ON—N-heterocyclic compound or a ON—C-heterocyclic compound.

24. The composition of claim 22, wherein compound comprising at least one O$_2$N—O—, O$_2$N—N—, O$_2$N—S— or O$_2$N—C— group is an O$_2$N—O-polypeptide, an O$_2$N—N-polypeptide, an O$_2$N—S-polypeptide, an O$_2$N—C-polypeptide, an O$_2$N—O-amino acid, O$_2$N—N-amino acid, O$_2$N—S-amino acid, an O$_2$N—C-amino acid, an O$_2$N—O-sugar, an O$_2$N—N-sugar, O$_2$N—S-sugar, an O$_2$N—C-sugar, an O$_2$N—O-oligonucleotide, an O$_2$N—N-oligonucleotide, an O$_2$N—S-oligonucleotide, an O$_2$N—C-oligonucleotide, a straight or branched, saturated or unsaturated, aliphatic or aromatic, substituted or unsubstituted O$_2$N—O-hydrocarbon, a straight or branched, saturated or unsaturated, aliphatic or aromatic, substituted or unsubstituted O$_2$N—N-hydrocarbon, a straight or branched, saturated or unsaturated, aliphatic or aromatic, substituted or unsubstituted O$_2$N—S-hydrocarbon, a straight or branched, saturated or unsaturated, aliphatic or aromatic, substituted or unsubstituted O$_2$N—C-hydrocarbon, an O$_2$N—O-heterocyclic compound, an O$_2$N—N-heterocyclic compound, an O$_2$N—S-heterocyclic compound or an O$_2$N—C-heterocyclic compound.

25. The composition of claim 18, wherein the at least one compound that donates, transfers, or releases nitric oxide, induces the production of endogenous nitric oxide or endothelium-derived relaxing factor, stimulates endogenous synthesis of nitrogen monoxide or is a substrate for nitric oxide synthase, is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, citrulline, omithine, glutamine, lysine, polypeptides comprising at least one of these amino acids or inhibitors of the enzyme arginase.

26. A method for treating a sexual dysfunction in a patient in need thereof comprising administering to the patient a therapeutically effective amount of the composition of claim 18.

27. The method of claim 26, wherein the patient is female.

28. The method of claim 26, wherein the patient is male.

29. The method of claim 26, wherein the composition is administered by intracavernosal injection, by transurethral application or topically.

30. The method of claim 29, wherein the composition is administered topically in the form of a cream, a spray, a lotion, a gel, an ointment, an emulsion, a foam, a coating for a condom, or a liposome composition.

31. A method for treating a cardiovascular disorder, a cerebrovascular disorder, hypertension, asthma, baldness, urinary incontinence, epilepsy, a gastrointestinal disorder, or an irritable bowel syndrome in a patient in need thereof comprising administering to the patient a therapeutically effective amount of the composition of claim 18.

32. The composition of claim 18, further comprising at least one vasoactive agent.

33. The composition of claim 32, wherein the vasoactive agent is a calcium channel blocker, an α-adrenergic receptor antagonist, a β-blocker, a phosphodiesterase inhibitor, adenosine, an ergot alkaloid, a vasoactive intestinal peptide, a prostaglandin, a dopamine agonist, a prostaglandin, an opioid antagonist, an endothelin antagonist, a thromboxane inhibitor or a mixture thereof.

34. A method for treating a sexual dysfunction in a patient in need thereof comprising administering to the patient a therapeutically effective amount of the composition of claim 32.

35. The method of claim 34, wherein the patient is female.

36. The method of claim 34, wherein the patient is male.

37. The method of claim 34, wherein the composition is administered by intracavernosal injection, by transurethral application or topically.

38. The method of claim 37, wherein the composition is administered topically in the form of a cream, a spray, a lotion, a gel, an ointment, an emulsion, a foam, a coating for a condom, or a liposome composition.

39. A method for treating a cardiovascular disorder, a cerebrovascular disorder, hypertension, asthma, baldness, urinary incontinence, epilepsy, a gastrointestinal disorder, or an irritable bowel syndrome in a patient in need thereof comprising administering to the patient a therapeutically effective amount of the composition of claim 32.

40. A kit comprising at least one compound of claim 1 and at least one compound that donates, transfers, or releases nitric oxide, induces the production of endogenous nitric oxide or endothelium-derived relaxing factor, stimulates endogenous synthesis of nitrogen monoxide or is a substrate for nitric oxide synthase, or a pharmaceutically acceptable salt thereof.

41. The kit of claim 40, further comprising at least one vasoactive agent.

42. The kit of claim 40, the compound of claim 1 and the compound that donates, transfers, or releases nitric oxide, induces the production of endogenous nitric oxide or endothelium-derived relaxing factor, stimulates endogenous synthesis of nitrogen monoxide or is a substrate for nitric oxide synthase are separate components in the kit.

43. The kit of claim 40, wherein the compound of claim 1 and the compound that donates, transfers, or releases nitric oxide, induces the production of endogenous nitric oxide or endothelium-derived relaxing factor, stimulates endogenous synthesis of nitrogen monoxide or is a substrate for nitric oxide synthase are in the form of a composition in the kit.

44. A compound of Formula (II), or a pharmaceutically acceptable salt thereof, having at least one NO group, at least one $NO_2$ group or at least one NO and $NO_2$ group, wherein the at least one NO group, the at least one $NO_2$ group or the at least one NO group and $NO_2$ group is linked to the compound of Formula (II) through an oxygen, sulfur or nitrogen atom, wherein the compound of Formula (II) is:

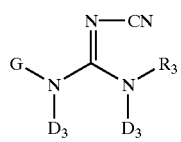

(II)

wherein
$R_3$ is a hydrogen, an alkyl, an aryl or an alkylaryl;
$D_3$ is a hydrogen;
G is:

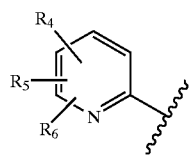

(1)

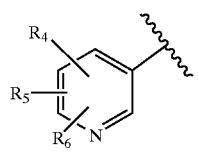

or (2)

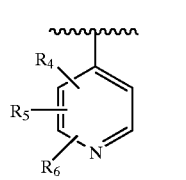

(3)

$R_4$, $R_5$, and $R_6$ are each independently a hydrogen, a halogen, a hydroxy, a lower alkyl, an alkoxy, a nitrile, a nitrite, a carboxyamido, a carboxylic ester, an alkylsulfinyl, an arylsulfinyl, an aminoalkyl, an alkylthio, or an arylthio; or $R_5$ and $R_6$ taken together are a group which forms a ring with the two carbon atoms to which they are attached, wherein the group is $-S(O)_t-(CH_2)_r-CH_2-$, $-C(O)Z-(CH_2)_o-CH_2$, or $-C(O)-CH_2-(CH_2)_o-Z-$;
t is an integer of 1 or 2;
r is an integer from 1 to 3;
Z is oxygen, $NR_7$ or $CH_2$; and
$R_7$ is hydrogen or $R_3$.

* * * * *